United States Patent [19]

Lednicer

[11] 4,113,866
[45] Sep. 12, 1978

[54] ANALGETIC COMPOUNDS, COMPOSITIONS AND PROCESS OF TREATMENT

[75] Inventor: Daniel Lednicer, Evansville, Ind.

[73] Assignee: The Upjohn Company, Kalamazoo, Mich.

[21] Appl. No.: 783,806

[22] Filed: Apr. 1, 1977

[51] Int. Cl.$^2$ ............... C07D 295/12; A61K 31/535
[52] U.S. Cl. .................. 424/248.56; 424/248.55;
424/250; 424/267; 424/274; 424/330;
260/293.78; 260/376 SL; 260/326.8 S; 260/570
S; 260/570 CA; 260/570.8 R; 260/570.9;
544/166; 544/395
[58] Field of Search ............ 544/166; 424/248.55,
424/248.56

[56] References Cited

U.S. PATENT DOCUMENTS 2,828,313  3/1958  Scholz et al. ............... 260/293.65

Primary Examiner—Henry R. Jiles
Assistant Examiner—R. W. Ramsuer
Attorney, Agent, or Firm—John J. Killinger; Roman Saliwanchik

[57] ABSTRACT

Novel compounds of the formula:

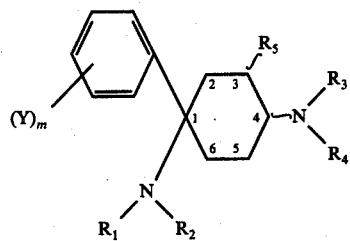

wherein $R_1$ is a variable consisting of hydrogen, alkyl of from 1 to 8 carbon atoms, $CH_2$-alkenyl wherein alkenyl is from 2 to 4 carbon atoms, inclusive, cycloalkyl of from 3 to 6 carbon atoms, inclusive, cycloalkylmethyl of from 3 to 6 carbon atoms, inclusive; $R_2$ is a variable consisting of hydrogen, alkyl of from 1 to 8 carbon atoms, inclusive, with the proviso that $R_1$ and $R_2$ cannot both be hydrogen at the same time; Y is a variable consisting of alkyl of from 1 to 4 carbon atoms, inclusive, halogen, trifluoromethyl, hydroxy, alkanoyloxy from 2 to 5 carbon atoms, inclusive, alkoxy of from 1 to 4 carbon atoms, inclusive, cycloalkyloxy of from 3 to 6 carbon atoms, inclusive, benzyloxy; m is an integer 0, 1, 2; $R_5$ is a variable consisting of hydrogen and alkyl of from 1 to 4 carbon atoms, inclusive; $R_3$ is a variable consisting of alkyl of from 1 to 4 carbon atoms, inclusive; $R_4$ is a variable consisting of alkyl of from 1 to 4 carbon atoms, inclusive, $CH_2$-alkenyl wherein alkenyl is of from 2 to 4 carbon atoms, inclusive, and arylalkyl wherein alkyl is from 1 to 4 carbon atoms, inclusive, and aryl is

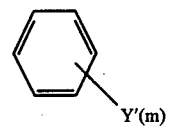

wherein Y' is $CF_3$, halogen, alkyl of 1 to 4 carbon atoms, inclusive, and alkoxy of from 1 to 4 carbon atoms, inclusive; and $R_3$ and $R_4$ when taken together with the nitrogen atom to which they are attached can form saturated heterocycles of from 5 to 7 ring members, a second hetero atom of said ring can be oxygen or nitrogen, e.g., morpholine, piperazine, and said heterocycles can be monosubstituted having a total of up to 9 carbon atoms, with the proviso that when

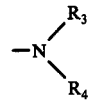

is pyrrolidinyl, then $m = 1, 2$, having analgetic activity in humans and animals are prepared in unit dosage forms. The compositions are useful in relieving pain by administering orally, parenterally, and rectally to humans and animals.

16 Claims, No Drawings

ANALGETIC COMPOUNDS, COMPOSITIONS AND PROCESS OF TREATMENT

CROSS REFERENCE TO RELATED APPLICTIONS

Application Ser. No. 692,589, filed June 3, 1976, now U.S. Pat. No. 4,065,573 discloses starting materials for the instant compounds and related analgetic compounds.

SUMMARY OF THE INVENTION

This invention pertains to some new organic chemical compounds that are active as analgesics. The invention is more particularly directed to some new 1,4-diamino-1-arylcyclohexanes and mono- or di- acid addition salts thereof; to an integral process for preparing the same; and to a method of, and formulations for relieving pain, regardless or origin, in animals and humans.

The new 1,4-diamino-1-arylcyclohexanes are represented in their free base form by the following formula I:

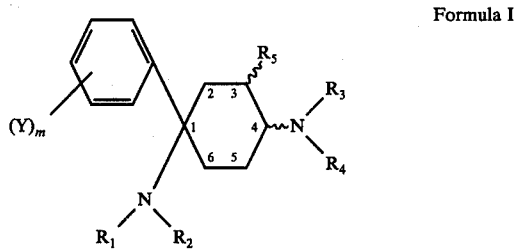

Formula I wherein $R_1$ is a variable consisting of hydrogen, alkyl of from 1 to 8 carbon atoms, $CH_2$-alkenyl wherein alkenyl is from 2 to 4 carbon atoms, inclusive, cycloalkyl of from 3 to 6 carbon atoms, inclusive, cycloalkylmethyl of from 3 to 6 carbon atoms, inclusive, $R_2$ is a variable consisting of hydrogen, alkyl of from 1 to 8 carbon atoms, inclusive, with the proviso that $R_1$ and $R_2$ cannot both be hydrogen at the same time; Y is a variable consisting of alkyl of from 4 to 4 carbon atoms, inclusive, halogen, trifluoromethyl, hydroxy, alkanoyloxy from 2 to 5 carbon atoms, inclusive, alkoxy of from 1 to 4 carbon atoms, inclusive, cycloalkyloxy of from 3 to 6 carbon atoms, inclusive, benzyloxy; $m$ is an integer 0, 1, 2; $R_5$ is a variable consisting of hydrogen and alkyl of from 1 to 4 carbon atoms, inclusive; $R_3$ is a variable consisting of alkyl of from 1 to 4 carbon atoms, inclusive; $R_4$ is a variable consisting of alkyl of from 1 to 4 carbon atoms, inclusive, $CH_2$-alkenyl wherein alkenyl is from 2 to 4 carbon atoms, inclusive, and arylalkyl wherein alkyl is from 1 to 4 carbon atoms, inclusive, and aryl is

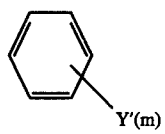

wherein $Y' = CF_3$, halogen, alkyl of 1 to 4 carbon atoms, inclusive, and alkoxy of from 1 to 4 carbon atoms, inclusive; and $R_3$ and $R_4$ when taken together with the nitrogen atom to which they are attached can form saturated heterocycles of from 5 to 7 ring members, one of said ring members can be a heteroatom such as oxygen or nitrogen, and said heterocycles can be monosubstituted having a total of up to 9 carbon atoms, with the proviso that when

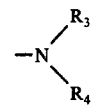

is pyrrolidinyl, then $m = 1, 2$.

DETAILED DESCRIPTION OF THE INVENTION

As stated, the invention includes the acid addition salts of the new, free base 1,4-diamino-1-arylcyclohexanes of Formula I. For the analgesic action discovered, the preferred acid addition salts will be the physiologically acceptable ones. This not only means that the anion of the salt should not interfere with the analgesic action of the characteristic molecule as a free base, but it should also be free from undesirable side effects and toxic action at the dosages administered.

In standard laboratory animal tests for analgesia the preferred compounds of this invention show analgetic activity of a similar order to meperidine hydrochloride.

The physiologically acceptable acid addition salts useful for pharmacologic purposes, e.g., analgesia, are obtained by neutralizing the free bases with acids according to conventional procedures. For example, the free base compounds can be treated with at least a stoichiometric amount of an acid; and depending upon the nature of the solvent employed, the desired acid salt will precipitate spontaneously or can be made to precipitate by the addition of a solvent in which the acid salt is insoluble. Acid addition salts can also be prepared metathetically by reacting one acid addition salt with an acid which is stronger than the anion of the salt.

Representative, suitable acids for physiologically acceptable acid addition salts include mineral acids such as sulfuric, hydrochloric, hydrobromic, nitric, and phosphoric; and organic acids such as acetic, propionic, benzoic, p-toluenesulfonic, salicylic, pamoic, tartaric, citric, and succinic.

On occasion, the free bases or their acid addition salts in their crystalline state are isolated as solvates, i.e., with a discreet quantity of solvent such as water, ethanol, and the like, associated physically and thus removable without effective alteration of the chemical entity per se.

The free base compounds of the invention as depicted structurally by Formula I are prepared by heating and reacting a 4-amino-4-arylcyclohexanone with a secondary amine in the presence of acid catalyst and an inert organic solvent medium. p-Toluenesulfonic acid is a preferred catalyst, and the heating is preferably in the range of 80° to to 120° C. although higher and lower temperatures can be used. Representative suitable organic solvent media include benzene (preferred), toluene and xylene. The reflux temperature of the reaction mixture is convenient, and water produced by the reaction can be removed as it is formed as the benzene:water azeotrope.

The reaction product is the enamine, and any secondary amine could be used. Titanium trichloride can be used as catalyst, in the case of less reactive secondary amines.

The enamine is reduced to the desired 4-amino product with, for example, sodium borohydride in alchol, or diborane in aprotic solvents such as tetrahydrofuran or ether. The 1,4-diamine can exist as cis and trans stereoisomers. The substituent at the 3-position ($R_5$) can also exist in a cis or trans configuration relative to the 1- or 4-amino functionalities. These possibilities are denoted by the wavy bonds in Formula I (~). The symbol is intended to include both stereoconfigurations.

$R_5$ when other than hydrogen can be introduced into position 3 by reaction at the ketone stage with alkyl lithium in inert solvent followed by reaction with alkyl halide, preferably alkyl iodide.

The compounds of Formula I when prepared by the methods disclosed herein are found in a cis-trans mixture; one of the isomers is present in greater proportion than the other, and these can be separated by conventional means. The means of separation practiced in this invention is chromatography on a silica gel column using as eluants solvent mixtures of increasing polarity. The active (analgetic) stereoisomer is the less polar component of the product mixture.

When $R_5$ is a substituent other than hydrogen, three ring carbon atoms (numbers 1, 3 and 4) possess chirality (are asymmetric), and thus the compound can also exhibit optical isomerism (dextro and levo isomers for each stereoconfiguration). These optical isomers can be resolved by methods known in the art, using commercially available optically active acids, e.g., (+)-tartaric acid, or bis-p-toluoyltartaric acid.

The product diamines of Formula I are recovered and purified by conventional techniques of solvent evaporation, chromatography, and crystallization. Variations of the recovery and purification procedures described as the best embodiments in this description of the invention will be apparent to those skilled in organic preparations.

Notwithstanding the fact thay any secondary amine can be employed in the process of the invention, for purposes of analgesia a more limited scope of secondary amines is contemplated. Accordingly,

can be dialkylamino, e.g., dimethylamino, diethylamino, dipropylamino, dibutylamino, methylisopropylamino, methyl-n-butylamino and the like.

In addition, when $R_3$ = methyl, then $R_4$ can be $CH_2$-alkenyl, e.g., 2-propenyl (allyl), 2-butenyl, and the like. Further the

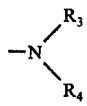

group can be a saturated heterocyclic group as defined; some representative examples include 1-pyrrolidinyl, alkylpyrrolidinyl, for example, 3-butylpyrrolidinyl; piperidino, alkylpiperidino, for example, 3-methylpiperidino, 4-methylpiperidino, 3-isopropylpiperidino, and 4-tert-butylpiperidino; 4-alkylpiperazinyl, for example, 4-methylpiperazinyl, and 4-isopropylpiperazinyl; morpholino, alkylmorpholino, for example, 3-isobutylmorpholino.

A preferred group of compounds for the purposes of this invention is that wherein the heterocycle is morpholino, $R_1$ and $R_2$ are alkyl of from 1 to 4 carbon atoms, inclusive, Y is halogen, hydroxy, or alkanoyloxy of from 2 to 5 carbon atoms, inclusive, and m is zero or 1. Preferred compounds are 1-(p-chlorophenyl)-1-dimethylamino-4-N-morpholinocyclohexane and 1-phenyl-1-dimethylamino-4-N-morphoinocyclohexane.

The term "halogen" is intended to include chlorine, bromine, and fluorine.

The term "aryl" as used herein means phenyl and substituted phenyl, for example, 4-chlorophenyl, 3-benzyloxyphenyl, 2-tolyl, 3,4-diethylphenyl, 2,4-dimethoxyphenyl, and the like.

"Alkanoyloxy of 2-5 carbon atoms, inclusive" means, for example, acetoxy, butyroxy and such groups.

The limited term "alkyl from 1 to 4 carbon atoms, inclusive," means methyl, ethyl, propyl, butyl, and isomeric forms thereof, e.g., tert-butyl, i-propyl. An "alkyl" of 1 to 8 carbon atoms, inclusive, encompasses groups such as methyl, propyl, butyl, hexyl, octyl, and isomers thereof. "Alkoxy of from 1 to 5 carbon atoms, inclusive," is similarly defined to mean methoxy, ethoxy, butoxy, pentoxy, i-propoxy, and the like.

The precursor 4-amino-4-arylcyclohexanones of this invention are themselves new compounds and they can be prepared as described in the Preparations. An alternative preparation is also described which is quicker and more efficient.

PREPARATION I

Synthesis of precursor 4-(p-Chlorophenyl)-4-dimethylaminocyclohexanone amd antecedent compounds Part a — Preparation of first antecedent, the Dimethyl diester of 4-(p-chlorophenyl)-4-cyanopimelic acid A mixture consisting of 25.0 gm. (0.165 mole) p-chlorophenyl acetonitrile, 77 ml. methyl acrylate, and 80 ml. tert-butyl alcohol is heated to the reflux temperature. The source of heat is removed, and a mixture consisting of 25 ml. of 40 percent methanolic tetramethylammonium hydroxide (Triton B ®) and 37 ml. tert-butyl alcohol is quickly added. Heating at the reflux temperature is resumed and continued for four (4) hours. The reaction mixture is allowed to cool, and is then diluted with water and benzene. The organic solvent and aqueous phases that form are separated and the aqueous phase discarded. The organic phase is washed successively with 2.5 N hydrochloric acid, water, and finally with brine. It is then dried over magnesium sulfate. The organic solvent is removed by evaporation under reduced pressure, and the residue thus obtained is distilled under reduced pressure. The initial pressure is 40 mm mercury at which pressure any remaining methyl acrylate and other volatile components are removed. There is then obtained 38.06 gm. (71.4% yield) of the dimethyl ester of 4-(p-chlorophenyl)-4-cyanopimelic acid as an oil having a boiling point at 186° to 191° C. (0.05 mm Hg.).

Part b — Preparation of second antecedent, 2-Carbomethoxy-4-(p-chlorophenyl)-4-cyanocyclohexanone A reaction mixture consisting of 34.97 gm. (0.108 mole) dimethyl ester of 4-(p-chlorophenyl)-4-cyanopimelic acid (prepared in Part a, above) dissolved in 700 ml.

tetrahydrofuran with 24.4 gm. (0.218 mole) potassium tertbutoxide added is heated at the reflux temperature for 4½ hours. After cooling, the reaction mixture is chilled in an ice-bath and 175 ml. 2.5 N acetic acid is added. The organic and aqueous phases separate and the organic phase is recovered. It is diluted with 600 ml. benzene before being washed successively with aqueous sodium bicarbonate, water, and brine. The organic solvents are then removed by distillation under reduced pressure. There is thus obtained 30.2 gm. (96% yield) of 2-carbomethoxy-4-(p-chlorophenyl)-4-cyanocyclohexanone having a melting point at 139° to 143° C.

Part c — Preparation of third antecedent, 4-(p-chlorophenyl)-4-cyanocyclohexanone A reaction mixture consisting of 29.8 gm. (0.102 mole) of 2-carbomethoxy-4-(p-chlorophenyl)-4-cyanocyclohexanone (prepared in Part b, above), 550 ml. glacial acetic acid, and 330 ml. 10 percent sulfuric acid is heated on a steam bath at about 100° C. for 24 hours. The mixture is stirred continuously. After cooling, the mixture is diluted with 1000 ml. water, and extracted with benzene. The benzene phase is recovered and washed successively with water, with aqueous sodium bicarbonate, and with brine. The benzene is then removed by evaporation under reduced pressure to give a solid residue. The solid residue is recrystallized from diethyl ether to give 12.13 gm. (82% yield) of 4-(p-chlorophenyl)-4-cyanocyclohexanone having a melting point at 94.5° to 97° C.

Analysis: Calc'd. for $C_{13}H_{12}ClNO$: C, 66.81; H, 5.18; N, 5.99. Found: C, 67.03; H, 5.16; N, 5.95.

Part d — Preparation of fourth antecedent, 4-(p-chlorophenyl)-4-cyanocyclohexanone, ethylene ketal A reaction mixture consisting of 19.49 gm. (0.084 mole) of 4-(p-chlorophenyl)-4-cyanocyclohexanone (prepared in Part c, above), 4.8 ml. (5.33 gm.) (0.086 mole) ethylene glycol. 0.21 Gm. p-toluenesulfonic acid, and 150 ml. benzene is heated at the reflux temperature in a reaction vessel equipped with a Dean and Stark trap for 6 hours. The reaction solution is then allowed to cool before washing it successively with aqueous sodium bicarbonate, with water, and with brine. The washed solution is then taken to dryness by evaporation of the benzene. The solid residue thus obtained is crystallized from hexane to give 21.87 gm. (79% yield) of 4-(chlorophenyl)-4-cyanocyclohexanone ethylene ketal having a melting point at 124° to 126.5° C.

Analysis: Calc'd. for $C_{15}H_{16}ClNO_2$: C, 64.96; H, 5.81; N, 5.04. Found: C, 64.77; H, 5.81; N, 4.92.

Part e — Preparation of fifth antecedent, 4-Carboxy-4-(p-chlorophenyl)cyclohexanone, ethylene ketal A reaction mixture consisting of 21.87 gm. (0.079 mole) 4-(p-chlorophenyl)-4-cyanocyclohexanone, ethylene ketal (prepared in Part d, above), 22.0 gm. (0.39 mole) potassium hydroxide and 220 ml. ethylene glycol is heated at the reflux temperature for 16 hours. After cooling and diluting with water, the solution is chilled in an ice-bath, layered with diethyl ether and cautiously acidified with concentrated hydrochloric acid. The ether layer is recovered and the acidic aqueous solution extracted two more times with ether. The ether extracts are combined and washed with brine before removing the ether by a evaporation. The residue thus obtained is recrystallized from a mixture of methylene chloride and technical hexane to give 19.26 gm. (82% yield) of 4-carboxy-4-(p-chlorophenyl)-cyclohexanone, ethylene ketal having a melting point at 162.5° to 164.5° C.

Analysis: Calc'd. for $C_{15}H_{17}ClO_4$: C, 60.71; H, 5.78; Cl, 11.95. Found: C, 61.01; H, 5.77; Cl, 12.12.

Part f — Preparation of sixth antecedent, 4-(p-Chlorophenyl)-4-isocyanatocyclohexanone, ethylene ketal To a mixture consisting of 15.79 gm. (0.0532 mole) 4-carboxy-4-(p-chlorophenyl)cyclohexanone, ethylene ketal (prepared in Part e, above) 7.4 ml. (5.36 gm., 0.532 mole) triethylamine, and 135 ml. anisole is added 14.7 gm. (0.534 mole) diphenylphosphonic azide. This reaction mixture is then heated at 90° to 100° C. in an oil bath for 2 hours. The volatile components are then removed by evaporation under reduced pressure, and the gummy residue thus obtained is chromatographed on a 1500 ml. column of silica gel. The column is eluted with a mixture of ethyl acetate and technical hexanes (in proportion of 1:9). After combining those fractions shown by thin layer chromatography (TLC) to contain product and removing the solvents by evaporation under reduced pressure, there is obtained 7.75 gm. of crude product. Recrystallization from petroleum ether gives 6.72 gm. (43% yield) of 4-p-chlorophenyl)-4-isocyanatocyclohexanone, ethylene ketal having a melting point at 76.5° to 80° C.

Analysis: Calc'd. for $C_{15}H_{16}ClNO_3$: C, 61.33; H, 5.49; N, 4.77. Found: C, 61.44; H, 5.50; N, 4.59.

Part g — Preparation of seventh antecedent, 4-(p-chlorophenyl)-4-methylaminocyclohexanone, ethylene ketal A solution consisting of 6.62 gm. (0.0226 mole) 4-(p-chlorophenyl)-4-isocyanatocyclohexanone, ethylene ketal (prepared in Part f, above) in 50 ml. tetrahydrofuran is mixed with a suspension of 1.29 gm. (0.045 mole) lithium aluminum hydride in 20 ml. tetrahydrofuran and the resulting reaction mixtue heated at the reflux temperature for 4 hours. After cooling, followed by chilling in an ice bath, 1.3 ml. water, 1.3 ml. 15 percent sodium hydroxide, and finally another 3.9 ml. water are added, successively. A gelatinuous precipitate forms; the mixture is filtered. The filtrate is saved, and the volatile components are removed by evaporation under reduced pressure. The residue thus obtained is recrystallized from petroleum ether to give 5.78 gm. (91% yield) of 4-p-chlorophenyl)-4-methylaminocyclohexanone, ethylene ketal that has a melting point at 63.5° to 66.5° C.

Analysis: Calc'd. for $C_{15}H_{20}ClNO_2$: C, 63.93; H, 7.15; N, 4.97. Found: C, 64.14; H, 7.32; N, 5.15.

Part h — Preparation of eighth antecedent compound, 4-(p-chlorophenyl)-4-dimethylaminocyclohexanone, ethylene ketal free base and the hydrochloride thereof A reaction solution consisting of 5.68 gm. (0.0201 mole) 4-(p-chlorophenyl)-4-methylaminocyclohexanone, ethylene ketal (prepared in Part g, above), 22 ml. 37 percent formalin, and 75 ml. methanol is heated at the reflux temperature for 4 hours, after which heating the solution is allowed to cool and is then chilled in an ice-bath. Small portions of sodium borohydride are cautiously added with stirring to a total of 2.89 gm. (0.076 mole). Stirring is continued for 2 hours at 25° C. when the solution is concentrated by removing most of the solvent under reduced pressure. The concentrate is diluted with methylene chloride and water. The aqueous phase that separates is discarded, and the organic phase is washed successively with water and then with brine. The methylene chloride solvent is then removed by evaporation under reduced pressure. The residue thus obtained is dissolved in the formalin and methanol as initially, heated at the reflux temperature, cooled in an ice bath, and treated again with the sodium borohydride as previously. Following the same work-up as described, the crude 4-(p-chlorophenyl)-4-dimethylaminocyclohexanone, ethylene ketal free base from the removal of the methylene chloride is dissolved in a small amount of diethyl ether, and the ether solution is treated with 3 N hydrogen chloride in ether. A precipitate forms which is recrystallized from methylene chloride to give 3.96 gm. (59% yield) of 4-p-chlorophenyl)-4-dimethylaminocyclohexanone, ethylene ketal hydrochloride having a melting point at 261° to 262° C. (with decomposition).

Analysis: Calc'd. for $C_{16}H_{22}NO_2 \cdot HCl$: C, 57.83; H, 6.98; N, 4.27. Found: C, 58.10; H, 7.01; N, 4.41.

Part i - Preparation of an object compound, 4-(p-chlorophenyl)-4-dimethylaminocyclohexanone A reaction solution consisting of 4.52 gm. (0.0136 mole) of 4-(p-chlorophenyl)-4-dimethylaminocyclohexanone, ethylene ketal hydrochloride (prepared in Part h, above), 22.5 ml. 2.5 N hydrochloric acid, and 45 ml. methanol is set aside at 25° C. for 48 hours. The methanol medium is substantially removed by evaporation under reduced pressure to give a concentrate that is made strongly basic by additions of 50 percent aqueous sodium hydroxide. A precipitate forms which is collected on a filter and dissolved in diethyl ether. This ether solution is washed successively with water and with brine before removing all the ether by evaporation under reduced pressure. The residue thus obtained is recrystallized from diethyl ether to give 2.30 gm. (70% yield) of 4-(p-chlorophenyl)-4-dimethylaminocyclohexanone having a melting point at 108° to 111° C.

Analysis: Calc'd. for $C_{24}H_{28}ClNO$: C, 66.79; H, 7.21; N, 5.57. Found: C, 67.10; H, 7.36; N, 5.42.

PREPARATION II

Synthesis of precursor
4-Dimethylamino-4-phenylcyclohexanone and antecedent compounds Part a - Preparation of first antecedent compound, the Dimethyl ester of 4-cyano-4-phenylpimelic acid Following the procedure of Preparation I, Part a, but substituting 29.26 gm. (0.25 mole) of phenyl acetonitrile for the 25.0 gm. of p-chlorophenyl acetonitrile and using 116 ml. methyl acrylate, 120 ml. tert-butyl alcohol, 38 ml. of the 40 percent methanolic tetramethylammonium hydroxide, and 56 ml. tert-butyl alcohol instead of the 77 ml., the 80 ml., the 25 ml., and the 37 ml. quantities stated, respectively, and carrying out the final distillation pressure at 0.45 mm of mercury, there is prepared 55.15 gm. (70% yield) of the dimethyl diester of 4-cyano-4-phenylpimelic acid as an oil having a boiling range from 183° to 186° C.

Part b — Preparation of second antecedent compound, 2-carbomethoxy-4-cyano-4-phenylcyclohexanone Following the procedure of Preparation I, Part b, but substituting 2.0 gm. (0.0069 mole) of the dimethyl ester of 4-cyano-4-phenylpimelic acid (prepared in Part a, above) for the 34.97 gm. of the dimethyl ester of 4-p-chlorophenyl)-4-cyanopimelic acid and using 45 ml. of the tetrahydrofuran, 1.57 gm. (0.014 mole) of the potassium tertbutoxide, and 10 ml. of the 2.5 N acetic acid instead of the 700 ml., the 24.4 gm., and the 175 ml., respectively, there is obtained a residue which upon recrystallization from technical hexane gives 1.07 gm. (60% yield) of the desired 2-carbomethoxy-4-cyano-4-phenylcyclohexanone having a melting point at 79.5° to 81.5° C.

Analysis: Calc'd. for $C_{15}H_{15}NO_3$: C, 70.02; H, 5.88; N, 5.44. Found: C, 69.77; H, 5.88; N, 5.54.

Part c — Preparation of third antecedent compound, 4-cyano-4-phenylcyclohexanone Following the procedure of Preparation I, Part c, but substituting 44.7 gm. (0.174 mole) of 2-carbomethoxy-4-cyano-4-phenylcyclohexanone (prepared as in Part b, above) for the 29.8 gm. of the 2-carbomethoxy-4-(p-chlorophenyl)-4-cyanocyclohexanone and using 1200 ml. of the glacial acetic acid, and 600 ml. of the 10 percent aqueous sulfuric acid instead of the 660 ml. and the 330 ml., respectively, and finally recrystallizing the residual solid from a mixture of ethyl acetate and hexane, there is obtained 25.75 gm. (75% yield) of the desired 4-cyano4-phenylcyclohexanone having a melting range from 112° to 115.5° C.

Part d — Preparation of fourth antecedent compound, 4-cyano-4-phenylcyclohexanone, ethylene ketal Following the procedure of Preparation I, part d, but substituting 10.0 gm. (0.05 mole) of 4-cyano-4-phenylcyclohexanone (prepared in Part c, above) for the 4-(p-chlorophenyl)-4-cyanocyclohexanone and using 2.85 ml. (3.17 gm., 0.051 mole) of the ethylene glycol, 0.12 gm. of the p-toluenesulfonic acid, and 90 ml. of the benzene solvent instead of the 4.8 ml., the 0.21 gm., and the 150 ml., respectively, there is obtained 11.27 gm. (92% yield) of the desired 4-cyano-4-phenylcyclohexanone, ethylene ketal as a crystalline solid having a melting range of 120° to 122.5° C.

Analysis: Calc'd. for $C_{15}H_{17}NO_2$: C, 74.05; H, 7.04; N, 5.76. Found: C, 74.10; H, 6.98; N, 5.77.

Part e — Preparation of fifth antecedent compound, 4-carboxy-4-phenylcyclohexanone, ethylene ketal Following the procedure of Preparation I, Part e, but substituting 11.27 gm. (0.0464 mole) of 4-cyano-4-phenylcyclohexanone, ethylene ketal (prepared in Part d, above) for the 21.87 gm. of the 4-(p-chlorophenyl)-4-cyanocyclohexanone, ethylene ketal, and using 11.3 gm. (0.2 mole) of the potassium hydroxide, and 90 ml. of the ethylene glycol instead of the 22.0 gm. and 220 ml., respectively, there is obtained 10.51 gm. (86% yield) of the desired 4-carboxy-4-phenylcyclohexanone, ethylene ketal as a crystalline solid having a melting range from 136° to 140.5° C.

Analysis: Calc'd. for $C_{15}H_{18}O_4$: C, 68.68; H, 6.92. Found: C, 68.27; H, 6.90.

Part f — Preparation of sixth antecedent compound, 4-isocyanato-4-phenylcyclohexanone, ethylene ketal Following the procedure of Preparation I, Part f, but substituting 2.62 gm. (0.01 mole) of 4-carboxy-4phenylcyclohexanone ethylene ketal (prepared in Part e, above) for the 15.79 gm. of the 4-carboxy-4-(p-chlorophenyl)cyclohexanone, ethylene ketal and using 1.38 ml. (1.01 gm., 0.01 mole) of the triethylamine, 25 ml. of the anisole, 2.75 gm. of the diphenylphosphonic azide, and a 400 ml. silica gel column instead of the 7.4 ml. (5.36 gm., 0.532 mole), the 135 ml., the 14.7 gm., and the 1500 ml. column, respectively, there is obtained 1.94 gm. (75% yield) of the desired 4-isocyanato-4-phenylcyclohexanone, ethylene ketal which has a melting range from 47° to 50° C. An analytical sample recrystalized from petroleum ether has a melting range from 48° to 50° C.

Analysis: Calc'd. for $C_{15}H_{17}NO_3$: C, 69.48; H, 6.61; N, 5.40. Found: C, 69.56; H, 7.01; N, 5.39.

Part g — Preparation of seventh antecedent compound, 4-methylamino-4-phenylcyclohexanone, ethylene ketal hydrochloride A solution consisting of 0.96 gm. (0.0037 mole) of 4-isocyanato-4-phenylcyclohexanone, ethylene ketal (prepared in Part f, above) and 15 ml. tetrahydrofuran is added to a suspension prepared by dispersing 0.20 gm. (0.0053 mole) lithium aluminum hydride in 5 ml. tetrahydrofuran. The resulting reaction mixture is heated at the reflux temperature with stirring for 4 hours. The mixture is then allowed to cool before chilling it in an ice-bath. To the chilled mixture is added 0.2 ml. water, 0.2 ml. 15 percent aqueous sodium hydroxide, and a further 0.6 ml. water. A gelatinous precipitate forms and the entire preparation is poured onto a filter. The filtrate is collected and the volatile components are removed by evaporation under reduced pressure. The residue thus obtained is dissolved in a small amount of diethyl ether and 3 N hydrogen chloride in ether is added to the solution in an amount judged to give the desired, insoluble acid addition salt. After collecting the crude salt on a filter and recrystallizing it from a mixture of methylene chloride and ethyl acetate, there is obtained 0.82 gm. (78% yield) of 4-methylamino-4-phenylcyclohexanone, ethylene ketal hydrochloride having a melting point at 243° to 245° C.

Analysis: Calc'd. for $C_{15}H_{22}ClNO_2$: C, 63.48; H, 7.82; N, 4.94. Found: C, 63.51; H, 7.89; N, 5.00.

Part h — Preparation of eighth intermediate compound, 4-Dimethylamino-4-phenylcyclohexanone, ethylene ketal hydrochloride A reaction solution consisting of the free base from 1.0 gm. (0.0035 mole) 4-methylamino-4-phenylcyclohexanone, ethylene ketal hydrochloride (prepared as in Part g, above), 3.6 ml. 37 percent formalin, and 12 ml. methanol is heated at the reflux temperature for 4 hours. This reaction mixture is allowed to cool to room temperature before chilling it in an ice-bath. Small portions of sodium borohydride are cautiously added with stirring to a total amount of 0.48 gm. (0.125 mole). Stirring is continued at 25° C. for 2 hours, and then the volatile solvents are removed by evaporation under reduced pressure. The residue thus obtained is dispersed in a mixture of methylene chloride and water and the liquids are allowed to separate. The methylene chloride phase is recovered and washed with water and then with brine. After removing the methylene chloride solvent by evaporation under reduced pressure, the residue is dissolved in a small amount of ether. A solution of hydrogen chloride in ether (3N) is added so as to produce the hydrochloride acid addition salt which precipitates out. The precipitate is collected on a filter and recrystallized from a mixture of methylene chloride and ethyl acetate to give 0.72 gm. (68% yield) of the desired final product, 4-dimethylamino-4-phenylcyclohexanone, ethylene ketal hydrochloride having a melting range from 226° to 229° C. An analytical sample is obtained by recrystallization from methylene chloride:ethyl acetate and has a melting range from 236° to 238° C.

Analysis: Calc'd. for $C_{16}H_{23}NO_2 \cdot HCl$: C, 64.52; H, 8.12; N, 4.70. Found: C, 64.47; H, 7.85; N, 4.92.

Part i — Preparation of object compound, 4-Dimethylamino-4-phenylcyclohexanone

Following the procedure of Preparation I, Part i, but substituting 13.66 gm. (0.052 mole) 4-dimethylamino-4-phenylcyclohexanone, ethylene ketal (prepared in Preparation I, Part h, above) for the 4.52 gm. of the 4-(p-chlorophenyl)-4-dimethylaminocyclohexanone, ethylene ketal hydrochloride and using 70 ml. 2.5 N hydrochloric acid and 14 ml. methanol instead of the 22.5 ml. and 45 ml. respectively, there is prepared 7.76 gm. (69% yield) of 4-dimethylamino-4-phenylcyclohexanone having a melting point at 98° to 99.5° C. An analytical sample has a melting range at 100° to 103° C.

Analysis: Calc'd. for $C_{14}H_{19}NO$: C, 77.38; H, 8.81; N, 6.45. Found: C, 77.39; H, 8.86; N, 6.41.

PREPARATION III

Alternative preparation for the compound 4-(p-chlorophenyl)-4-dimethylaminocyclohexanone, ethylene ketal free base and the hydrochloride thereof Part a — Preparation of the first antecedent compound, Cyclohexane-1,4-dione, ethylene ketal A reaction mixture consisting of 10 gm. (0.085 mole) 4-hydroxycyclohexanone, 4.75 ml. ethylene glycol, 0.20 gm. p-toluenesulfonic acid, and 100 ml. benzene is heated at the reflux temperature in a reaction vessel fitted with a Dean and Stark trap for 2 hours. After the reaction mixture cools, it is washed first with water and then with brine. The benzene is then removed by evaporation under reduced pressure giving the intermediate 4-hydroxycyclohexane monoketal as a viscous oil weighing 14.12 gm. The 4-hydroxycyclohexane monoketal is dissolved in 100 ml. methylene chloride and added with stirring to a suspension consisting of 55.0 gm. chromium trioxide (predried for 24 hours under reduced pressure over phosphorous pentoxide), one liter dry methylene chloride, and 52.8 gm. 3,5-dimethylpyrazole. After continued stirring for 10 minutes this dark reaction mixture is poured onto a two liter column of silica gel. When the reaction mixture has been completely absorbed, the chromatogram is developed with a 1:1 mixture of ethyl acetate and technical hexane (Skellysolve B — a mixture of isomeric hexanes having a boiling range between 60° and 70° C.). Fractions which are found by thin layer chromatography (TLC) to contain the product are collected and combined, after which the solvents are removed by evaporation under reduced pressure. The crystals thus obtained are recrystallized from technical hexane, and there is thus obtained 10.82 gm. (91% yield) of the desired cyclohexane-1,4-dione, ethylene monoketal having a melting point at 68° to 69° C. (The literature value is 71.5° to 72.5° C.).

Part b — Preparation of second antecedent compound, 4-Cyano-4-dimethylaminocyclohexanone, ethylene ketal A reaction mixture consisting of 3.0 gm. (0.019 mole) of the cyclohexane-1,4-dione, ethylene ketal prepared in Part A, above, 3.0 gm. potassium cyanide, 4.6 gm. dimethylamine hydrochloride, 3.0 ml. methanol, and 25 ml. saturated aqueous dimethylamine is stirred at 25° C. for 48 hours. The reaction mixture is then extracted successively with five-40 ml. portions of diethyl ether. The ether extracts are combined and the ether removed by evaporation under reduced pressure. The residue thus obtained is dissolved in methylene chloride. Some small amount of water present is separated, and the organic solvent portion conserved for removal of the methylene chloride by evaporation under reduced pressure. The residual solid thus obtained is recrystallized from technical hexane to give 3.6 gm. (78% yield) of the desired intermediate 4-cyano-4-dimethylaminocyclohexanone, ethylene ketal having a melting point at 79° to 81° C.

Analysis: Calc'd. for $C_{11}H_{17}N_2O_2$: C, 62.83; H, 8.63; N, 13.33. Found: C, 62.92; H, 8.66; N, 13.58.

Part c — Preparation of object compound, 4-(p-Chlorophenyl)-4-dimethylaminocyclohexanone, ethylene ketal hydrochloride A Grignard reagent is prepared from 2.73 gm. of p-chlorobromobenzene, 0.35 gm. magnesium and 30 ml. tetrahydrofuran; 1.50 gm. (0.0071 mole) of 4-cyano-4-dimethylaminocyclohexanone, ethylene ketal (prepared in Part b, above) is dissolved in 40 ml. tetrahydrofuran and added to it. The reaction mixture is heated for 3 days at the reflux temperature. It is then cooled, chilled in an ice bath, and 20 ml. saturated ammonium chloride in benzene is added. The liquid is separated. It is washed initially with water and then with brine. Finally, the solvents are removed by evaporation under reduced pressure. The residue thus obtained is dissolved in diethyl ether and 4 N ethereal hydrogen chloride is added until precipitation is complete. The salt thus obtained is collected on a filter as a gummy material. It is suspended in methylene chloride and 1 N aqueous sodium hydroxide is added. The organic layer is separated and the methylene chloride removed by evaporation under reduced pressure. The residue thus obtained is transferred to a 200 ml. column of silica gel and the chromatogram developed with methylene chloride containing 3% methanol. Fractions which are shown by thin layer chromatography (TLC) to contain the product are collected and combined. The solvent is removed by evaporation under reduced pressure and the residue is dissolved in diethyl ether. The ether solution is treated with 4 N ethereal hydrogen chloride until precipitation of the desired 4-(p-chlorophenyl)-4-dimethylaminocyclohexanone ethylene ketal hydrochloride is complete. The precipitate is collected on a filter and crystallized from a mixture of methylene chloride and ethyl acetate to give 0.80 gm. (34% yield) of pure 4-(p-chlorophenyl)-4-dimethylaminocyclohexanone ethylene ketal hydrochloride having a melting point at 252° to 254° C.

PREPARATION IV

Preparation of 4-(m-hydroxyphenyl)-4-dimethylaminocyclohexanone

Part a

A reaction solution consisting of 5.0 gm. (0.029 mole) m-bromophenol, 5.0 gm. dihydropyran, 0.30 gm. p-toluenesulfonic acid, and 80 ml. anhydrous diethyl ether is stirred at 25° C. for 4 hours. The mixture is washed successively with 25 ml. portions of 1 N aqueous sodium hydroxide, with water, and with brine. The thus washed organic layer is taken to dryness by removing the solvent by evaporation under reduced pressure. There is thus obtained 7.42 gm. of m-(tetrahydropyranyloxy)bromobenzene which is converted to the corresponding Grignard reagent by adding 0.70 gm. magnesium and 60 ml. tetrahydrofuran. To this Grignard is added 1.50 gm. (0.0071 mole) of 4-cyano-4-dimethylaminocyclohexanone ethylene ketal (prepared in Preparation III, Part b, above) dissolved in 30 ml. tetrahydrofuran. This reaction mixture is heated at the reflux temperature for 22 hours. After cooling, the mixture is treated with 10 ml. saturated aqueous ammonium chloride and benzene. The organic solvent portion is initially washed with water and then with brine. The organic solvent is then removed by evaporation under reduced pressure. The residue thus obtained is dissolved in diethyl ether and treated with 4 N ethereal hydrogen chloride until precipitation of the hydrochloride salt is complete. The salt is collected on a filter and then suspended in 25 ml. water containing 1 ml. 2.5 N hydrochloride acid. The acidified mixture is stirred at 25° C. for one hour, when sodium bicarbonate (solid) is added until the pH is 8. This slightly basic mixture is extracted thoroughly with diethyl ether. The ether extracts are combined and the ether removed by evaporation under reduced pressure. The residue thus obtained is transferred to a column of silica gel 1 inch in cross section by 48" long. The chromatogram is developed with a solvent medium consisting of 0.5 percent ammonia and 7.5 percent methanol in chloroform. Fractions which are shown by thin layer chromatography (TLC) to contain product are collected and combined. The solvent is removed by evaporation under reduced pressure to give 0.96 gm. (48% yield) of crude 4-(m-hydroxyphenyl)-4-dimethylaminocyclohexanone, ethylene ketal having a melting point at 169° to 175° C. An analytical sample is obtained by recrystallization from a mixture of ethyl acetate and cyclohexane. The melting point is 175° to 177° C.

Analysis: Calc'd. for $C_{16}H_{23}NO_3$: C, 69.28; H, 8.36; N, 5.05. Found: C, 69.08; H, 8.13; N, 5.02.

Part b — Preparation of 4-(m-hydroxyphenyl)-4-dimethylaminocyclohexanone

A reaction mixture consisting of 1.92 gm. (0.0069 mole) of 4-(m-hydroxyphenyl)-4-dimethylaminocyclohexanone, ethylene ketal (prepared in Part a, above), 15 ml. 2.5 N hydrochloric acid, and 30 ml. methanol is stirred continuously for 3 days (72 hours). The bulk of the solvent is then removed by evaporation under reduced pressure, and solid sodium bicarbonate is added until the pH is 8. This slightly basic mixture is then extracted with six 20 ml. portions of chloroform. The extracts are combined and the chloroform is removed by evaporation under reduced pressure. The residue thus obtained is recrystallized from a mixture of acetone and technical hexane to give 0.48 gm. (30% yield) of 4-(m-hydroxyphenyl)-4-dimethylaminocyclohexanone having a melting point at 127° to 130° C.

Analysis: Cal'd. for $C_{14}H_{19}NO_2$: C, 72.07; H, 8.21; N, 6.01. Found: C, 72.02; H, 8.13; N, 5.87.

PREPARATION V

Preparation of 4-(m-anisyl)-4-dimethylaminocyclohexanone

Part a — Preparation of precursor, the Dimethyl ester of 4-(m-anisyl)-4-cyanopimelic acid Following the procedure of Preparation I, Part a, but substituting 25.0 gm. (0.17 mole) m-anisyl acetonitrile for the 25.0 gm. of the p-chlorophenyl acetonitrile and using 79 ml. methyl acrylate, 27 ml. of the 40% methanolic tetramethylammonium hydroxide with 38 ml. tert-butyl alcohol, instead of the 77 ml., the 25 ml., and 37 ml., respectively, and decreasing the final distillation pressure to 0.07 mm, there is prepared 30.34 gm. (56% yield) of the dimethyl ester of 4-(m-anisyl)-4-cyanopimelic acid as an oil having a boiling range from 180° to 187° C.

Part b — Preparation of first intermediate, 4-(m-anisyl)-4-carbomethoxy-4-cyanocyclohexanone Following the procedure of Preparation I, Part b, but substituting 30.34 gm. (0.0951 mole) of the dimethyl ester of 4-(m-anisyl)-4-cyanopimelic acid (prepared in Part a, above) for the 34.97 gm. of the dimethyl ester of 4-(p-chlorophenyl)-4-cyanopimelic acid and using 620 ml. of the tetrahydrofuran, 21.3 gm. (0.19 mole) of the potassium tert-butoxide, and 150 ml. of the 2.5 N glacial acetic acid instead of the 700 ml., the 24.4 gm. (0.218 mole), and the 175 ml., respectively, there is prepared 29.1 gm. (99% yield) of 4-(m-anisyl)-2-carbomethoxy-4-cyanocyclohexanone as a gum.

Part c — Preparation of second intermediate, 4-(m-anisyl)-4-cyanocyclohexanone

Following the same procedure as described in Preparation I, Part c, but substituting 29.1 gm. (0.01 mole) of 4-(m-anisyl)-2-carbomethoxy-4-cyanocyclohexanone (prepared in Part b, above) for the 29.8 gm. of 2-carbomethoxy-4-(p-chlorophenyl)-4-cyanocyclohexanone, there is obtained 14.93 gm. (64% yield) of 4-(m-anisyl)-4-cyanocyclohexanone having a melting range at 72° to 76° C.

Analysis: Calc'd for $C_{14}H_{15}NO_2$: C, 73,34; H, 6.59; N, 6.11. Found: C, 73.68; H, 6.76; N, 6.21.

Part d — Preparation of third intermediate, 4-(m-anisyl)-4-cyanocyclohexanone, ethylene ketal Following the procedure of Preparation I, Part d, but substituting 14.93 gm. (0.065 mole) of 4-(m-anisyl)-4-cyanocyclohexanone (prepared in Part c, above) for the 19.49 gm. of the 4-(p-chlorophenyl)-4-cyanocyclohexanone, using 4.0 ml. ethylene glycol, 0.16 gm. p-toluenesulfonic acid, and 110 ml. benzene instead of the 4.8 ml., the 0.21 gm., and the 150 ml., respectively, and recrystallizing from technical hexane instead of cyclohexane, there is obtained 15.24 gm. (92% yield) of 4-(m-anisyl)-4-cyanocyclohexanone, ethylene ketal melting at 70° to 72° C.

Analysis: Calc'd. for $C_{16}H_{19}NO_3$: C, 70.31; H, 7.01; N, 5.13. Found: C, 70.09; H, 7.07; N, 4.96.

Part e — Preparation of fourth intermediate 4-(m-anisyl)-4-carboxycyclohexanone, ethylene ketal Following the procedure of Preparation I, Part e, but substituting 16.24 gm. (0.059 mole) of 4-(m-anisyl)-4-cyanocyclohexanone, ethylene ketal (prepared in Part d, above) for the 21.87 gm. of the 4-carboxy-4-(p-chlorophenyl)cyclohexanone, ethylene ketal and using 7.83 gm. (0.19 mole) sodium hydroxide and 110 ml. ethylene glycol instead of the 22.0 gm. (0.39 mole) potassium hydroxide and 220 ml., respectively, there is obtained, without recrystallization, 17.31 gm. (99% yield) of 4-(m-anisyl)-4-carboxycyclohexanone, ethylene ketal having a melting range at 102° to 107° C.

Part f — Preparation of fifth intermediate, 4-(m-anisyl)-4-isocyanatocyclohexanone, ethylene ketal Following the procedure of Preparation I, Part f, but substituting the 17.31 gm. (0.059 mole) of 4-(m-anisyl)-4-carboxycyclohexanone, ethylene ketal (prepared in Part e, above) for the 15.79 gm. of the 4-carboxy-4-(p-chlorophenyl)cyclohexanone, ethylene ketal and using 6.0 ml. (8.23 gm., 0.059 mole) triethylamine, 160 ml. anisole, and 16.31 gm. diphenylphosphonic azide instead of the 7.4 ml., the 135 ml., and the 14.7 gm., respectively, there is obtained after elution of the silica gel column with a 1.5 percent mixture of ethyl acetate in methylene chloride, 4.07 gm. of 4-(m-anisyl)-4-isocyanatocyclohexanone ethylene ketal.

Part g — Preparation of sixth intermediate 4-(m-anisyl)-4-methylaminocyclohexanone, ethylene ketal hydrochloride Following the procedure of Preparation I, Part g, but substituting 4.07 gm. (0.014 mole) of 4-(m-anisyl)-4-isocyanatocyclohexanone, ethylene ketal (prepared in Part f, above) for the 6.62 gm. 4-(p-chlorophenyl)-4-isocyanatocyclohexanone, ethylene ketal and using 80 ml. tetrahydrofuran, 0.76 gm. (0.02 mole) lithium aluminum hydride, and 10 ml. tetrahydrofuran instead of the 50 ml., the 1.29 gm., and the 20 ml., adding 0.76 ml. water, 0.76 ml. of 15 percent aqueous sodium hydroxide, and 2.28 ml. water instead of the 1.3 ml., the 1.3 ml., and the 3.9 ml., respectively, there is obtained a corresponding residue from the filtrate that is dissolved in a small amount of diethyl ether. The ether solution is acidified with an equivalent amount of 3 N hydrogen chloride in ether. The hydrochloride acid addition salt that precipitates is collected on a filter and recrystallized from a mixture of methylene chloride and ethyl acetate to afford 3.10 gm. (71% yield) of 4-(m-anisyl)-4-methylaminocyclohexanone, ethylene ketal hydrochloride having a melting point at 238° to 239° C.

Analysis: Calc'd. for $C_{16}H_{23}NO_2 \cdot HCl$: C, 61.23; H, 7.71; N, 4.46. Found: C, 60.07; H, 7.52; N, 4.29.

Part h — Preparation of 4-(m-anisyl)-4-(dimethylamino)cyclohexanone, ethylene ketal hydrochloride Following the procedure of Preparation I, Part h, but substituting the free base from 3.10 gm. (0.0099 mole) of 4-(m-anisyl)-4-methylaminocyclohexanone ethylene ketal hydrochloride (prepared in Part g, above) for the 4.68 gm. of the 4-(p-chlorophenyl)-4-methylaminocyclohexanone, ethylene ketal and using 7.5 ml. of 37 percent formalin, 22.5 ml. methanol, and adding 0.91 gm. sodium borohydride instead of the 22 ml., the 75 ml., and the 2.89 gm., respectively, there is obtained a hydrochloride precipitate that upon recrystallization from a mixture of methylene chloride and ethyl acetate gives 2.21 gm. (68% yield) of 4-(m-anisyl)-4-(dimethylamino)cyclohexanone, ethylene ketal hydrochloride having a melting point at 184° to 185.5° C.

Analysis: Calc'd. for $C_{17}H_{25}NO_3 \cdot HCl$: C, 62.28; H, 7.99; N, 4.27. Found: C, 62.11; H, 8.24; N, 4.21.

Part i — Preparation of 4-(m-anisyl)-4-dimethylaminocyclohexanone

Following the procedure of Preparation I, Part i, but substituting 1.71 gm. (0.0052 mole) of 4-(m-anisyl)-4-dimethylaminocyclohexanone, ethylene ketal hydrochloride (prepared in Part h, above) for the 4-(p-chlorophenyl)-4-dimethylaminocyclohexanone, ethylene ketal hydrochloride, 7.5 ml. of 2.5 N hydrochloric acid for the 22.5 ml., and 15 ml. methanol for the 45 ml., there is prepared (after recrystallization from petroleum ether instead of diethyl ether) 0.54 gm. (45% yield) of 4-(m-anisyl)-4-dimethylaminocyclohexanone as the free base having a melting point at 57° to 59° C.

Analysis: Calc'd. for $C_{15}H_{21}NO_2$: C, 72.84; H, 8.56; N, 5.66. Found: C, 72.88; H, 8.47; N, 5.72.

PREPARATION VI

Preparation of 4-(m-acetoxyphenyl)-4-(methyl-n-butylamino)cyclohexanone

Part a — 4-Cyano-4-(m-hydroxyphenyl)cyclohexan-1-one

To an ice-cooled solution of 10.0 g. (0.044 mole) of 4-cyano-4-(m-anisyl)cyclohexan-1-one prepared in Preparation V, Part c, in 125 ml. methylene chloride there is added dropwise 13 ml. of boron tribromide. Following 4 hours stirring in the cold the mixture is poured onto ice and diluted with 50 ml. chloroform. The organic layer is washed with water, aqueous sodium bicarbonate and brine, and taken to dryness. The residual solid is recrystallized from acetone:Skellysolve B to give 7.60 gm. of product, m.p. 130°–133° C.

Analysis: Calc'd. for $C_{13}H_{13}NO_2$: C, 72.54; H, 6.09; N, 6.51. Found: C, 72.50; H, 6.14; N, 6.35.

Part b — 4-Cyano-4-(m-hydroxyphenyl)cyclohexan-1-one, ethylene ketal

A mixture of 8.80 g., (0.041 mole) of 4-cyano-4-(m-hydroxyphenyl)cyclohexan-1-one, 2.50 ml. ethylene glycol and 0.26 gm. 1-toluenesulfonic acid in 170 ml. benzene is heated at reflux under a Dean-Stark trap for 4 hours. The mixture is then allowed to cool, washed with aqueous sodium bicarbonate and taken to dryness. The residual solid is recrystallized from methylene chloride:Skellysolve B to give 9.85 g. of the ketal, m.p. 109°–110.5° C.

Analysis: Calc'd. for $C_{15}H_{17}NO_3$: C, 69.48; H, 6.61; N, 5.32. Found: C, 69.23; H, 6.69; N, 5.32.

Part c — 4-Cyano-4-(m-benzyloxyphenyl)cyclohexan-1-one, ethylene ketal

To a solution of 9.85 gm. of 4-cyano-4-(m-hydroxyphenyl)cyclohexan-1-one, ethylene ketal in 40 ml. DMF and 80 ml. benzene there is added 1.85 gm. of a 50% dispersion of sodium hydride in mineral oil. The mixture is stirred for 15 mins. at room temperature and 1 hour at reflux. Benzyl chloride (6.53 gm.) is then added, the mixture is heated for an additional 4 hours and allowed to cool. The reaction mixture is washed in turn with water and brine and taken to dryness. The residual solid is recrystallized from ether:petroleum ether to give 11.70 gm. of product, m.p. 67°–69° C.

Analysis: Calc'd. for $C_{22}H_{23}NO_3$:C, 75.62; H, 6.63; N, 4.01. Found: C, 75.34; H, 6.66; N, 4.01.

Part d — 4-(m-benzyloxyphenyl)cyclohexan-1-one-4-carboxylic acid, ethylene ketal Part d — 4-(m-benzyloxyphenyl)cyclohexan-1-one-4-carboxylic acid, ethylene ketal A mixture of 7.00 gm. (0.020 mole) of 4-cyano-4-(m-benzyloxyphenyl)cyclohexan-1-one, ethylene ketal and 1.20 gm. sodium hydroxide in 50 ml. ethylene glycol is heated at reflux for 17 hours. The solution is allowed to cool, diluted to 300 ml. with water and covered with 100 ml. ether. The aqueous layer is acidified with 5 ml. concentrated hydrochloric acid and the organic layer separated. The aqueous layer is then extracted with 100 ml. portions of ether and methylene chloride. The extracts are combined, washed with water and brine and taken to dryness. There is obtained 7.22 gm. of acid, m.p. 108°–110.5° C. A small sample is recrystallized from ether to give the analytical sample, m.p. 118.5°–120.5° C.

Analysis: Calc'd. for $C_{22}H_{24}O_5$: C, 71.72; H, 6.57. Found: C, 71.80; H, 6.89.

Part e — 4-(m-Benzyloxyphenyl)-4-(methylamino)-cyclohexan-1-one, ethylene ketal

A mixture of 7.22 gm. (0.020 mole) of 4-(m-benzyloxyphenyl)cyclohexan-1-one-4-carboxylic acid, ethylene ketal, 5.52 gm. of diphenylphosphonic azide and 2.8 ml. triethylamine in 50 ml. anisole is heated in an oil bath at 90° C. for 2 hours. The bulk of the solvent is then removed in vacuum and the residue chromatographed over 600 ml. silica gel. The column is eluted with 2% ethyl acetate in methylene chloride and those fractions which contain product as determined by TLC are combined. There is obtained 4.97 gm. of the intermediate isocyanate as an oil.

A solution of the product obtained above in 80 ml. THF is added to 0.78 gm. lithium aluminum hydride in 10 ml. THF. Following 6 hours heating at reflux the mixture is cooled in ice bath and treated in turn with 0.7 ml. water, 0.8 ml. 15% sodium hydroxide and 2.4 ml. water. The inorganic gel is separated on a filter and the filtrate taken to dryness. The residual solid is recrystallized from petroleum ether to afford 3.31 g. of product, m.p. 64°–66° C.

Analysis: Calc'd. for $C_{22}H_{27}NO_3$: C, 74.75; H, 7.70; N, 3.96. Found: C, 75.03; H, 7.53; N, 3.93.

Part f — 4-(methyl-n-butylamino)-4-(m-benzyloxyphenyl)-cyclohexan-1-one, ethylene ketal To an ice cold solution of 3.31 gm. (9.4 mmole) of 4-methylamino-4-(m-benzyloxyphenyl)cyclohexan-1-one, ethylene ketal and 1.30 ml. triethylamine in 40 ml. THF there is added dropwise 1.0 gm. (1.10 ml.) butyryl chloride. Following 6 hours' standing in the cold the bulk of the solvent is removed in vacuum. The residual is diluted with ice-water and ether. The organic layer is separated and washed in turn with water, saturated sodium bicarbonate and brine. The solution is taken to dryness to give the amide as a gum. Infrared spectrum is consistent with structure assigned (absorption at 1660 cm.$^{-1}$). A solution of the crude amide obtained above in 80 ml. THF is added to a suspension of 0.60 gm. lithium aluminum hydride in 10 ml. THF. Following 6 hour' heating at reflux the mixture is cooled in ice and treated in turn with 0.60 ml. water, 0.50 ml. 15% sodium hydroxide and 1.5 ml. water. The inorganic gel is collected on a filter and the filtrate taken to dryness. There is obtained 3.50 gm. of 4-(methyl-n-butylamino)-4-(m-benzyloxyphenyl)cyclohexanone, ethylene ketal as an amorphous gum which shows a single spot on TLC.

Part g — Preparation of 4-(methyl-n-butylamino)-4-(m-benzyloxyphenyl)cyclohexanone Following the procedure of Preparation I, Part i, but substituting 4-(methyl-n-butylamino)-4-(m-benzyloxyphenyl)cyclohexanone, ethylene ketal for 4-(p-chlorophenyl)-4-dimethylaminocyclohexanone, ethylene ketal hydrochloride there is obtained 4-(methyl-n-butylamino)-4-(m-benzyloxyphenyl)cyclohexanone.

Part h — 4-(methyl-n-butylamino)-4-(m-hydroxyphenyl)cyclohexan-1-one, ethylene ketal hydrochloride A mixture of 3.56 gm. of 4-(m-benzyloxyphenyl)-4-(methyl-n-butylamino)cyclohexanone (Preparation VI, Part f), 3.6 ml. 3 N etheral hydrogen chloride and 1.78 gm. 10% palladium on charcoal in 150 ml. ethyl acetate is shaken in an atmosphere of hydrogen for 18 hours. The catalyst and some precipitated product are then collected on a filter. The collected solid is washed thoroughly with chloroform. The combined filtrate and washes are then taken to dryness. The residual solid is recrystallized from methylene chloride:acetone to give 2.00 gm. of crystalline product, m.p. 208°–210° C.

Part i — Preparation of 4-(m-hydroxyphenyl)-4-(methyl-n-butylamino)cyclohexanone Following the procedure of Preparation I, Part i, but substituting 4-(m-hydroxyphenyl)-4-(methyl-n-butylamino)cyclohexan-1-one, ethylene ketal hydrochloride (prepared in Part h, above) for the 4-(p-chlorophenyl)-4-dimethylaminocyclohexanone, ethylene ketal hydrochloride there is obtained the object compound, 4-(m-hydroxyphenyl)-4-(methyl-n-butylamino)cyclohexanone.

Part j

Following the procedure of Preparation XIII, but substituting 4-(m-hydroxyphenyl)-4-(methyl-n-butylamino)cyclohexanone (prepared in Preparation IV, Part i) for 4-(m-hydroxyphenyl)-4-(dimethylamino)cyclohexanone there is obtained the desired 4-(m-acetoxyphenyl)-4-(methyl-n-butylamino)cyclohexanone as the hydrochloride.

Analysis: Calc'd. for $C_{19}H_{27}NO_3 \cdot HCl \cdot \frac{1}{2}H_2O$: C, 62.36; H, 8.17; N, 3.82. Found: C, 62.07; H, 7.81; N, 3.80.

PREPARATION VIIA

Preparation of 4-(p-chlorophenyl)-2-methyl-4-dimethylaminocyclohexanone

A solution consisting of 0.51 gm. (0.005 mole) diisopropylamine in 10 ml. tetrahydrofuran is chilled in an ice: methanol bath and 3 ml. of 1.68N butyllithium in pentane is added. To this mixture is then added a solution consisting of 1.25 gm. (0.005 mole) 4(p-chlorophenyl)-4-dimethylaminocyclohexanone (prepared in Preparation I, above) in 20 ml. tetrahydrofuran. After 5 min. stirring, 1.42 gm. methyl iodide is added. The reaction mixture is stirred for another 30 min. in the cold, and then it is allowed to warm up to 25° C. Stirring is continued for 2½ hours when 20 ml. saturated aqueous ammonium chloride is added. Benzene is also added. The organic solvent phase is separated, washed initially with water and then with brine. The organic solvents are removed by evaporation under reduced pressure. The residue thus obtained is transferred to a chromatographic column containing 200 ml. silica gel. The chromatogram is developed with 2 liters of a mixture of 3% methanol in methylene chloride followed by 2 liters of a mixture of 5% methanol in methylene chloride. Fractions which are shown by TLC to contain product are collected and combined. The solvents are removed by evaporation under reduced pressure giving the desired 4-(p-chlorophenyl)-2-methyl-4-dimethylaminocyclohexanone. The compound is recrystallized from diethyl ether to give an analytical sample having a melting point at 110° to 111° C. This is recognized to be the cis isomer with respect to the 4-amino substituent, by NMR spectroscopy.

Analysis: Calc'd. for $C_{15}H_{20}ClNO$: C, 67.78; H, 7.59; N, 5.27. Found: C, 67.75; H, 7.59; N, 5.56.

The corresponding trans isomer is obtained from subsequent fractions eluted from the same column. It is recrystallized from a mixture of diethyl ether and technical hexane to give 0.52 gm. of the isomer having a melting point at 103° to 105° C.

PREPARATION VIIB

Following the same procedure as in Preparation VIIA, but substituting, e.g., ethyl iodide, n-propyl iodide, and n-butyl iodide for methyl iodide, there are prepared the corresponding
4-(p-chlorophenyl)-2-ethyl-4-dimethylaminocyclohexanone,
4-(p-chlorophenyl)-4-dimethylamino-2-n-propylcyclohexanone, and
2-n-butyl-4-(p-chlorophenyl)-4-dimethylaminocyclohexanone, respectively.

PREPARATION VIII

Part a

Following the procedure as described in Preparation III, Part b, but separately substituting diethylamine, di-n-propylamino, di-n-butylamine, N-n-propyl-N-2-butenylamine, N-methyl-N-cyclopropylamine, and N-allyl-N-cyclopropylmethylamine, as the hydrochlorides, for dimethylamine hydrochloride, there are prepared the corresponding intermediates:

4-cyano-4-diethylaminocyclohexanone, ethylene ketal,
4-cyano-4-dipropylaminocyclohexanone, ethylene ketal,
4-cyano-4-di-n-butylaminocyclohexanone, ethylene ketal,
4-cyano-4-(N-propyl-N-2-butenylamino)cyclohexanone, ethylene ketal,
4-cyano-4-(N-methyl-N-cyclopropylamino)cyclohexanone, ethylene ketal,
4-cyano-4-(N-allyl-N-cyclopropylmethylamino)cyclohexanone, ethylene ketal.

Part b

Following the procedure as described in Preparation III, Part c, but separately substituting such intermediate prepared in Part a (above) for the 4-cyano-4-dimethylaminohexanone, ethylene ketal, there are prepared the corresponding object compounds:
4-(p-chlorophenyl)-4-diethylaminocyclohexanone, ethylene ketal hydrochloride,
4-(p-chlorophenyl)-4-di-n-propylaminocyclohexanone, ethylene ketal hydrochloride,
4-(p-chlorophenyl)-4-di-n-butylaminocyclohexanone, ethylene ketal hydrochloride,
4-(p-chlorophenyl)-4-(N-propyl-N-2-butenylamino)cyclohexanone, ethylene ketal hydrochloride,
4-(p-chlorophenyl)-4-(N-methyl-N-cyclopropylamino)cyclohexanone, ethylene ketal hydrochloride, and
4-(p-chlorophenyl)-4-(N-allyl-N-cyclopropylmethylamino)cyclohexanone, ethylene ketal hydrochloride, respectively.

Part c

Following the procedure as described in Preparation IV, Part b, but separately substituting each intermediate prepared in Part b (above) for the 4-(m-hydroxyphenyl)-4-dimethylaminocyclohexanone, ethylene ketal, there are prepared the corresponding:
4-(p-chlorophenyl)-4-diethylaminocyclohexanone,
4-(p-chlorophenyl)-4-di-n-propylaminocyclohexanone,
4-(p-chlorophenyl)-4-di-n-butylaminocyclohexanone,
4-(p-chlorophenyl)-4-(N-propyl-N-2-butenylamino)cyclohexanone,
4-(p-chlorophenyl)-4-(N-methyl-N-cyclopropylamino)cyclohexanone, and
4-(p-chlorophenyl)-4-(N-allyl-N-cyclopropylmethylamino)cyclohexanone, respectively.

PREPARATION IX

Preparation of 2-Methyl-4-dimethylamino-4-(p-tolyl)cyclohexanone

A solution consisting of 1.02 gm. (0.010 mole) diisopropylamine in 20 ml. tetrahydrofuran is chilled in an ice-methanol bath before 6 ml. of 1.68 N butyllithium in pentane is added. To this mixture is then added a solution consisting of 2.31 gm. of 4-dimethylamino-4-(p-tolyl)cyclohexanone (prepared according to the procedure of Preparation I, Parts a through i, above) and 40 ml. tetrahydrofuran. Five minutes later, 2.82 gm. methyl iodide is added, and the mixture is stirred for 45 min. in the cold. It is allowed to warm up to 25° C. and stirring is continued for 5 hours, when the reaction mixture is diluted with a mixture of water and benzene. The organic layer is separated and washed first with water and then with brine. The organic solvents are removed by evaporation under reduced pressure, and the residual waxy solid thus obtained transferred to a column of silica gel 1 inch by 4 ft. The chromatogram is developed with a solvent medium consisting of 7.5% methanol in chloroform. Fractions which are shown by TLC to contain product are collected and combined. The solvent is removed by evaporation under reduced pressure, and the residue thus obtained is recrystallized from ether. There is thus obtained 1.01 gm. (39% yield) of the object compound 2-methyl-4-dimethylamino-4-(p-tolyl)cyclohexanone having a melting point at 102° to 104.5° C.

Analysis: Calc'd. for $C_{16}H_{23}NO$: C, 78.32; H, 9.45; N, 5.71. Found: C, 78.03; H, 9.51; N, 5.65.

PREPARATION X

Following the procedure of Preparation IX, above, but separately substituting each compound prepared in Preparation VIII, Part c for the 4-dimethylamino-4-(p-tolyl)cyclohexanone, there are prepared the corresponding object compounds:

4-(p-chlorophenyl)-4-diethylamino-2-methylcyclohexanone,
4-(p-chlorophenyl)-4-di-n-propylamino-2-methylcyclohexanone,
4-(p-chlorophenyl)-4-di-n-butylamino-2-methylcyclohexanone,
4-(p-chlorophenyl)-4-(N-propyl-N-2-butenylamino)-2-methylcyclohexanone,
4-(p-chlorophenyl)-4-(N-methyl-N-cyclopropylamino)-2-methylcyclohexanone, and
4-(p-chlorophenyl)-4-(N-allyl-N-cyclopropylmethylamino)-2-methylcyclohexanone, respectively.

PREPARATION XI

Following the procedure of Preparation I, Parts a through i, but initially substituting
p-methoxyphenyl acetonitrile,
o-methylphenyl acetonitrile,
p-bromophenyl acetonitrile,
p-ethoxyphenyl acetonitrile,
m-benzyloxyphenyl acetonitrile,
2,4-diethylphenyl acetonitrile,
3,5-dichlorophenyl acetonitrile,
(3-methoxy-4-chloro)phenyl acetonitrile,
(2-methyl-4-n-butyl)phenyl acetonitrile, for p-chlorophenyl acetonitrile, and subsequently substituting the respective intermediates at each step there are obtained the following compounds:
4-(p-methoxyphenyl)-4-dimethylaminocyclohexanone,
4-(p-methylphenyl)-4-dimethylaminocyclohexanone,
4-(p-bromophenyl)-4-dimethylaminocyclohexanone,
4-(p-ethoxyphenyl)-4-dimethylaminocyclohexanone,
4-(m-benzyloxyphenyl)-4-dimethylaminocyclohexanone,
4-(2,4-diethylphenyl)-4-dimethylaminocyclohexanone,
4-(3,5-dichlorophenyl)-4-dimethylaminocyclohexanone,
4-(3-methoxy-4-chlorophenyl)-4-dimethylaminocyclohexanone, and
4-(2-methyl-4-n-butylphenyl)-4-dimethylaminocyclohexanone, respectively.

PREPARATION XII

Following the procedure of Preparation VI (Part f) but substituting acetyl chloride, propionyl chloride, valeryl chloride, cyclopropanecarbonyl chloride, cyclohexylacetyl chloride, benzoyl chloride and 2,2-dimethylpropionyl chloride for butyryl chloride there are obtained the following compounds:
4-(methylethylamino)-4-(m-benzyloxyphenyl)cyclohexanone,
4-(methyl-n-propylamino)-4-(m-benzyloxyphenyl)cyclohexanone,
4-(n-pentylmethylamino)-4-(m-benzoyloxyphenyl)cyclohexanone,
4-(N-methyl-N-cyclopropylmethylamino)-4-(m-benzyloxyphenyl)cyclohexanone,
4-(N-$\beta$-cyclohexylethyl-N-methylamino)-4-(m-benzyloxyphenyl)cyclohexanone,
4-(N-benzyl-N-methylamino)-4-(m-benzyloxyphenyl)cyclohexanone, and
4-(N-methyl-N-pivalylamino)-4-(m-benzyloxyphenyl)cyclohexanone.

PREPARATION XIII

Preparation of 4-(m-acetoxyphenyl)-4-dimethylaminocyclohexan-1-one

To a solution of 0.96 gm. (4.1 mmole) of 4-(m-hydroxyphenyl)-4-dimethylaminocyclohexan-1-one (prepared in Preparation IV, Part b) in 20 ml. THF there is added 0.46 gm. (0.63 ml.) triethylamine and 0.46 gm. (0.42 ml.) acetic anhydride. Following 6 hours standing at room temperature the mixture is concentrated in vacuum and the residue diluted with ice:water. The precipitated gum is extracted with methylene chloride. The extract is washed with saturated sodium bicarbonate and brine and taken to dryness. The residue is chromatographed over a 1 inch × 48 inch column of TLC grade silica gel. These fractions shown by TLC to contain product are collected and taken to dryness. The solid which remains is recrystallized from petroleum ether to give 0.30 gm. of 4-(m-acetoxyphenyl)-4-dimethylamino-cyclohexan-1-one, m.p. 51°–53° C.

Analysis:
Calc'd. for $C_{16}H_{21}NO_3$: C, 69.79; H, 7.69; N, 5.09.
Found: C, 69.47; H, 7.89; N, 5.21.

EXAMPLE 1

Preparation of 1-dimethylamino-4-N-morpholino-1-phenylcyclohexane

A reaction mixture consisting of 2.31 gm. (0.01 mole) 4-dimethylamino-4-phenylcyclohexanone, (prepared in Preparation II, Part i, above) 0.87 gm. (0.01 mole) morpholine, 0.05 gm. p-toluenesulfonic acid, and 40 ml. benzene is heated at the reflux temperature, in a reaction vessel fitted with a Dean and Stark trap, for 6 hours. The benzene is then removed by evaporation under reduced pressure, and the residue is dissolved in 60 ml. absolute ethanol. To this solution is added 0.76 gm. (0.02 mole) sodium borohydride. The mixture is heated at the reflux temperature for 18 hours, after which interval the ethanol is allowed to evaporate. The residue thus obtained is dissolved in a mixture of diethyl ether and water. The ether phase is separated from the water phase, and washed with water followed by a brine solution. After removing the ether by evaporation, the gummy residue is transferred to a chromatographic column having 300 ml. silica gel. Development of the chromatogram with a solvent mixture consisting of methanol and methylene chloride (1:4) gives eluate fractions which are combined. Crystals form on evaporation. Two recrystallizations from aqueous methanol give 1.13 gm. (39% yield) of the object compound 1-dimethylamino-4-N-morpholino-1-phenylcyclohexane (less polar isomer) having a melting point at 84° to 85° C.

Analysis: Calc'd. for $C_{18}H_{28}N_2O$: C, 74.95; H, 9.78; N, 9.71. Found: C, 74.75; H, 9.83; N, 9.67.

Further development of the chromatogram with a solvent mixture consisting of methanol and methylene chloride in proportions of 2:3, respectively, gives fractions from which an oil is recovered. The oil thus obtained is dissolved in methanol and the methanolic solution is treated with an excess of 3N hydrogen chloride in diethyl ether. After removing the methanol and excess hydrogen chloride under reduced pressure, and recrystallizing the residue from a mixture of methanol and ethyl acetate, there is obtained 0.37 gm. of the more polar isomeric form of 1-dimethylamino-4-morpholino-1-phenylcyclohexane dihydrochloride as the monohydrate, having a melting point at 267° to 268° C.

Analysis: Calc'd. for $C_{18}H_{28}N_2O \cdot 2HCl \cdot H_2O$: C, 56.98; H, 8.50; N, 7.39. Found: C, 57.14; H, 8.82; N, 7.39.

EXAMPLE 2

Preparation of
1-dimethylamino-4-(1-pyrrolidinyl)-1-phenylcyclohexane dihydrochloride A reaction mixture consisting of 2.30 gm. ()0.010 mole) 4-dimethylamino-4-phenylcyclohexanone, (prepared in Preparation II, Part i, above) 2.0 ml. pyrrolidine, 0.50 gm. p-toluenesulfonic acid, and 40 ml. benzene is heated at the reflux temperature, in a vessel fitted with a Dean and Stark trap, for 18 hours. The benzene is then removed by evaporation under reduced pressure, and the residue is dissolved in 30 ml. tetrahydrofuran (THF). To this solution is added 0.76 gm. (0.020 mole) sodium borohydride in 10 ml. ethanol. This mixture is heated at the reflux temperature for 16 hours, after which interval, most of the ethanol is allowed to evaporate under reduced pressure. The ethanolic concentrate thus obtained is dispersed in a mixture of diethyl ether and water. After vigorous shaking, and after allowing the aqueous and organic phases to separate, the ether layer is recovered. It is washed first with water and then with brine. The ether is then removed by evaporation. The residue thus obtained is transferred for purposes of chromatographic purification onto a 250 ml. column of silica gel. The chromatogram is developed with a solvent mixture consisting of 1% ammonia and 10% methanol in methylene chloride. The first material obtained in the eluate is a waxy solid. It is dissolved in methanol and treated with an excess of 3 N ethereal hydrogen chloride. After removing the ether methanol and excess hydrogen chloride by evaporation, the residue is recrystallized two times from a mixture of methanol and ethyl acetate. There is thus obtained 0.86 gm. of 1-dimethylamino-4-(1-puyrrolidinyl)-1-phenylcyclohexane dihydrochloride monohydrate having a melting point at 200°–204° C.

Analysis:
Calc'd. for $C_{18}H_{28}N_2O \cdot 2HCl \cdot H_2O$: C, 59.49; H, 8.79; N, 7.71.
Found: C, 58.90; H, 8.79; N, 7.22.

The more polar isomer of the 1-dimethylamino-4-(1-pyrrolidinyl)-1-phenylcyclohexane free base is obtained by further elution of the column with the same solvent mixture. It is recovered from the eluate and recrystallized several times from aqueous methanol to give a 60.0 mg. amount which has a melting point at 83° to 84° C.

Analysis:
Calc'd. for $C_{18}H_{28}N_2$: C, 79.35; H, 10.36; N, 10.29.
Found: C, 79.36; H, 9.92; N, 10.01.

EXAMPLE 3

Preparation of
1-Dimethylamino-4-(N-piperidino)-1-phenylcyclohexane dihydrochloride A reaction mixture consisting of 2.30 gm. (0.01 mole) 4-dimethylamino-4-phenylcyclohexanone (prepared in Preparation II, Part i, above) 1.6 ml. piperidine, 0.05 gm. paratoluenesulfonic acid, and 40 ml. benzene is heated for 18 hours at the reflux temperature in a reaction vessel fitted with a Dean and Stark trap. The benzene is then removed by evaporation under reduced pressure. The residue thus obtained is dissolved in 25 ml. of THF that has been chilled to 0° C. To this solution is added 0.76 gm. (0.02 mole) sodium borohydride in 10 ml. ethanol. This reaction mixture is heated at the reflux temperature for another interval of 18 hours, after which the ethanol is substantially all removed by evaporation under reduced pressure. The concentrate thus obtained is dissolved in a mixture of diethyl ether and water. After vigorous mixing and shaking the organic and aqueous phases are allowed to separate, and the organic phase is recovered. It is washed first with water and then with brine. The ether is then allowed to evaporate. The residue thus obtained is transferred onto a 250 ml. column of silica gel in order to effect a chromatographic purification. The column is developed with a solvent system consisting of 15% methanol in methylene chloride with 1% ammonium hydroxide present.

The substance obtained from the first eluate fractions is recovered by evaporating the solvents under reduced pressure. It is dissolved in methanol and the methanolic solution is treated with 10 ml. of 3 N ethereal hydrogen chloride. After removing the methanol, diethyl ether, and excess hydrogen chloride by evaporation under reduced pressure, the residue is recrystallized from a mixture of methanol and ethyl acetate to give 1.92 gm. (53% yield) of 1-dimethylamino-4-piperidino-1-phenylcyclohexane dihydrochloride having a melting point at 245° to 246° C.

Analysis:
Calc'd. for $C_{19}H_{30}N_2 \cdot 2HCl$: C, 63.50; H, 8.98; N, 7.80.
Found: C, 63.25; H, 9.27; N, 7.72.

Further elution of the column with 40% methanol in methylene chloride containing 4% ammonium hydroxide affords a more polar isomer that upon recrystallization from aqueous methanol amounts to 90 mg. of 1-dimethylamino-4-(N-piperidino)-1-phenylcyclohexane free base having a melting point at 89° to 91° C.

Analysis:
Calc'd. for $C_{19}H_{30}N_2$: C, 79.66; H, 10.56; N, 9.78.
Found: C, 78.95; H, 10.74; N, 9.64.

EXAMPLE 4

Preparation of
1-(p-Chlorophenyl)-1-dimethylamino-4-N-morpholinocyclohexane

A reaction mixture consisting of 2.63 gm. (0.01 mole) 4-(p-chlorophenyl)-4-dimethylaminocyclohexanone (prepared as in Preparation I, Part i, above), 0.87 ml. morpholine, 0.05 gm. para-toluenesulfonic acid, and 40 ml. benzene is heated at the reflux temperature for 7 hours in a reaction vessel fitted with a Dean and Stark trap. The benzene is then removed by evaporation under reduced pressure. The residue thus obtained is dissolved in 10 ml. tetrahydrofuran, to which solution is added 0.76 gm. (0.02 mole) sodium borohydride in 35.0 ml. absolute ethanol. This reaction mixture is heated at the reflux temperature for 17 hours, after which heating the tetrahydrofuran and ethanol are removed by evaporation under pressure. The residue thus obtained is dispersed in a mixture of water and diethyl ether. After vigorous shaking and allowing the aqueous and organic phases to separate, the organic phase is recovered. It is washed first with water and then with brine. The ether is then allowed to evaporate. The residue thus obtained is transferred onto a 1 inch by 4 foot column of silica gel averaging 20 to 50 microns in size, for purposes of high pressure liquid chromatographic (HPLC) purification. The chromatogram is developed with a solvent system consisting of 5% methanol in chloroform with 1% triethylamine. The fractions of eluate containing the object compound yield a solid which is recrystallized from aqueous methanol to give 0.95 gm. (30% yield) of 1-(p-chlorophenyl)-1-dimethylamino-4-morpholinocyclohexane having a melting point at 103° to 105° C.

Analysis:
Calc'd. for $C_{18}H_{27}ClN_2O$: C, 66.95; H, 8.43; N, 8.68. Found: C, 66.73; H, 8.52; N, 8.54.

EXAMPLE 5

Preparation of 1-Dimethylamino-4-(N-allyl-N-methylamino)-1-(p-chlorophenyl)cyclohexane and its dihydrochloride hydrate A mixture of 1.50 gm. (6 mmole) of 4-(p-chlorophenyl)-4-dimethylaminocyclohexanone, 2.5 ml. N-allyl-N-methylamine and 0.05 gm. p-toluenesulfonic acid in 40 ml. benzene is stirred at reflux temperature under molecular sieve trap for 30 hours. The mixture is taken to dryness and the residue is dissolved in 25 ml. of tetrahydrofuran. To this ice-cooled solution is added 0.25 gm. of sodium borohydride in 25 ml. of ethanol. Following eighteen (18) hours' heating at reflux, the bulk of the solvent is removed under vacuum and the residue partitioned between water and ether as described in Example 4. The organic phase is washed sequentially with water and with brine and the ether is removed by evaporation. The residue is placed on a 1 inch by 48 inch silica gel column and eluted by high pressure liquid chromatography using a solvent system consisting of 0.5% ammonium hydroxide and 5% methanol in chloroform. The less polar isomer is eluted first; it is converted to the dihydrochloride salt by reaction with 3N alcoholic hydrogen chloride. The salt is recrystallized from a methanol-ethyl acetate solvent mixture to give 0.95 gm. (41% yield) of 1-(p-chlorophenyl)-1-dimethylamino-4-(N-methyl-N-allylamino)cyclohexane dihydrochloride hydrate having a melting point of 224°-226° C.

Analysis:
Calc'd. for $C_{18}H_{27}ClN.2HCl.H_2O$: C, 54.34; H, 7.85; N, 7.04. Found: C, 54.44; H, 7.80; N, 7.04.

Further elution of the chromatographic column with 10% methanol in chloroform gives the more polar isomer form. As with the less polar isomer, the dihydrochloride is prepared and recrystallized from a methanol-acetonitrile solvent mixture. A 0.20 gm. (8.7% yield) quantity of compound is obtained as the hemihydrate having a melting point of 253°-254° C.

Analysis: Calc'd. for $C_{18}H_{27}ClN.2HCl.1/2H_2O$: C, 55.60; H, 7.78; N, 7.21. Found: C, 55.54; H, 7.71; N, 7.46.

EXAMPLE 6

Following the procedure of Example 4, but separately substituting each of the intermediates prepared according to Preparation VIII for 4-(p-chlorophenyl)-4-dimethylaminocyclohexanone, and
methylethylamine,
N-allyl-N-propylamine,
N-β-phenethyl-N-methylamine,
N-(2-methoxy-4-chlorophenyl)-N-ethylamine,
N-(3,5-dimethylphenyl)-N-propylamine,
morpholine,
4-ethylpiperidine,
4-methylpiperazine,
3-propylpyrrolidine for morpholine, and reacting each amine independently with each ketone there are obtained the following compounds:
1-(p-chlorophenyl)-1-diethylamino-4-methylethylaminocyclohexane;
1-(p-chlorophenyl)-1-diethylamino-4-(N-allyl-N-propylamino)cyclohexane;
1-(p-chlorophenyl)-1-diethylamino-4-(N-β-phenethyl-N-methylamino)cyclohexane;
1-(p-chlorophenyl)-1-diethylamino-4-[N-(2-methoxy-4-chlorophenyl)-N-ethylamino]cyclohexane;
1-(p-chlorophenyl)-1-diethylamino-4-(N-3,5-dimethylphenyl-N-propylamino)cyclohexane;
1-(p-chlorophenyl)-1-diethylamino-4-N-morpholinocyclohexane;
1-(p-chlorophenyl)-1-diethylamino-4-(4-ethyl-N-piperidino)cyclohexane;
1-(p-chlorophenyl)-1-diethylamino-4-(4-methylpiperazino)cyclohexane; and
1-(p-chlorophenyl)-1-diethylamino-4-(3-propyl-N-pyrrolidino)cyclohexane;
1-(p-chlorophenyl)-1-di-n-propylamino-4-methylethylaminocyclohexane;
1-(p-chlorophenyl)-1-di-n-propylamino-4-(N-allyl-N-propylamino)cyclohexane;
1-(p-chlorophenyl)-1-di-n-propylamino-4-(N-β-phenethyl-N-methylamino)cyclohexane;
1-(p-chlorophenyl)-1-di-n-propylamino-4-[N-(2-methoxy-4-chlorophenyl)-N-ethylamino]cyclohexane;
1-(p-chlorophenyl)-1-di-n-propylamino-4-(N-3,4-dimethylphenyl-N-propylamino)cyclohexane;
1-(p-chlorophenyl)-1-di-n-propylamino-4-N-morpholinocyclohexane;
1-(p-chlorophenyl)-1-di-n-propylamino-4-(4-ethyl-N-piperidino)cyclohexane;
1-(p-chlorophenyl)-1-di-n-propylamino-4-(4-methylpiperazino)cyclohexane; and
1-(p-chlorophenyl)-1-di-n-propylamino-4-(3-propyl-N-pyrrolidino)cyclohexane;
1-(p-chlorophenyl)-1-di-n-butylamino-4-methylethylaminocyclohexane;
1-(p-chlorophenyl)-1-di-n-butylamino-4-(N-allyl-N-propylamino)cyclohexane;
1-(p-chlorophenyl)-1-di-n-butylamino-4-(N-β-phenethyl-N-methylamino)cyclohexane;
1-(p-chlorophenyl)-1-di-n-butylamino-4-[N-(2-methoxy-4-chlorophenyl)-N-ethylamino]cyclohexane;
1-(p-chlorophenyl)-1-di-n-butylamino-4-(N-3,5-dimethylphenyl-N-propylamino)cyclohexane;
1-(p-chlorophenyl)-1-di-n-butylamino-4-N-morpholinocyclohexane;

1-(p-chlorophenyl)-1-di-n-butylamino-4-(4-ethyl-N-piperidino)cyclohexane;

1-(p-chlorophenyl)-1-di-n-butylamino-4-(4-methylpiperazino)cyclohexane; and 1-(p-chlorophenyl)-1-di-n-butylamino-4-(3-propyl-N-pyrrolidino)cyclohexane;

1-(p-chlorophenyl)-1-(N-propyl-N-2-butenylamino)-4-methylethylaminocyclohexane;

1-(p-chlorophenyl)-1-(N-propyl-N-2-butenylamino)-4-(N-allyl-N-propylamino)cyclohexane;

1-(p-chlorophenyl)-1-(N-propyl-N-2-butenylamino)-4-(N-β-phenethyl-N-methylamino)cyclohexane;

1-(p-chlorophenyl)-1-(N-propyl-N-2-butenylamino)-4-[N-(2-methoxy-4-chlorophenyl)-N-ethylamino]cyclohexane;

1-(p-chlorophenyl)-1-(N-propyl-N-2-butenylamino)-4-(N-3,5-dimethylphenyl-N-propylamino)cyclohexane;

1-(p-chlorophenyl)-1-(N-propyl-N-2-butenylamino)-4-N-morpholinocyclohexane;

1-(p-chlorophenyl)-1-(N-propyl-N-2-butenylamino)-4-(4-ethyl-N-piperidino)cyclohexane;

1-(p-chlorophenyl)-1-(N-propyl-N-2-butenylamino)-4-(4-methylpiperazino)cyclohexane; and 1-(p-chlorophenyl)-1-(N-propyl-N-2-butenylamino)-4-(3-propyl-N-pyrrolidino)cyclohexane;

1-(p-chlorophenyl)-1-(N-methyl-N-cyclopropylamino)-4-methylethylaminocyclohexane;

1-(p-chlorophenyl)-1-(N-methyl-N-cyclopropylamino)-4-(N-allyl-N-propylamino)cyclohexane;

1-(p-chlorophenyl)-1-(N-methyl-N-cyclopropylamino)-4-(N-β-phenethyl-N-methylamino)cyclohexane;

1-(p-chlorophenyl)-1-(N-methyl-N-cyclopropylamino)-4-[N-(2-methoxy-4-chlorophenyl)-N-ethylamino]cyclohexane;

1-(p-chlorophenyl)-1-(N-methyl-N-cyclopropylamino)-4-(N-3,5-dimethylphenyl-N-propylamino)cyclohexane;

1-(p-chlorophenyl)-1-(N-methyl-N-cyclopropylamino)-4-N-morpholinocyclohexane;

1-(p-chlorophenyl)-1-(N-methyl-N-cyclopropylamino)-4-(4-ethyl-N-piperidino)cyclohexane;

1-(p-chlorophenyl)-1-(N-methyl-N-cyclopropylamino)-4-(4-methylpiperazino)cyclohexane; and 1-(p-chlorophenyl)-1-(N-methyl-N-cyclopropylamino)-4-(3-propyl-N-pyrrolidino)cyclohexane;

1-(p-chlorophenyl)-1-(N-allyl-N-cyclopropylmethylamino)-4-methylethylaminocyclohexane;

1-(p-chlorophenyl)-1-(N-allyl-N-cyclopropylmethylamino)-4-(N-allyl-N-propylamino)cyclohexane;

1-(p-chlorophenyl)-1-(N-allyl-N-cyclopropylmethylamino)-4-(N-β-phenethyl-N-methylamino)cyclohexane;

1-(p-chlorophenyl)-1-(N-allyl-N-cyclopropylmethylamino)-4-[N-(2-methoxy-4-chlorophenyl)-N-ethylamino]cyclohexane;

1-(p-chlorophenyl)-1-(N-allyl-N-cyclopropylmethylamino)-4-(N-3,5-dimethoxyphenyl-N-propylamino)cyclohexane;

1-(p-chlorophenyl)-1-(N-allyl-N-cyclopropylmethylamino)-4-N-morpholinocyclohexane;

1-(p-chlorophenyl)-1-(N-allyl-N-cyclopropylmethylamino)-4-(4-ethyl-N-piperidino)cyclohexane;

1-(p-chlorophenyl)-1-(N-allyl-N-cyclopropylmethylamino)-4-(4-methylpiperazino)cyclohexane; and 1-(p-chlorophenyl)-1-(N-allyl-N-cyclopropylmethylamino)-4-(3-propyl-N-pyrrolidino)cyclohexane.

EXAMPLE 7

Following the procedure of Example 4 but separately substituting each of the compounds prepared according to Preparations VIIB and X for 4-(p-chlorophenyl)-4-dimethylaminocyclohexanone and
methylethylamine,
N-allyl-N-propylamine,
N-β-phenethyl-N-methylamine,
N-(2-methoxy-4-chlorophenyl)-N-ethylamine,
N-(3,5-dimethylphenyl)-N-propylamine,
morpholine,
4-ethylpiperidine,
4-methylpiperazine,
3-propylpyrrolidine for morpholine, and reacting each amine independently with each ketone there are obtained the following compounds:

1-(p-chlorophenyl)-1-dimethylamino-3-ethyl-4-methylethylaminocyclohexane;

1-(p-chlorophenyl)-1-dimethylamino-3-ethyl-4-(N-allyl-N-propylamino)cyclohexane;

1-(p-chlorophenyl)-1-dimethylamino-3-ethyl-4-(N-β-phenethyl-N-methylamino)cyclohexane;

1-(p-chlorophenyl)-1-dimethylamino-3-ethyl-4-[N-(2-methoxy-4-chlorophenyl)-N-ethylamino]cyclohexane;

1-(p-chlorophenyl)-1-dimethylamino-3-ethyl-4-(N-3,5-dimethylphenyl-N-propylamino)cyclohexane;

1-(p-chlorophenyl)-1-dimethylamino-3-ethyl-4-N-morpholinocyclohexane;

1-(p-chlorophenyl)-1-dimethylamino-3-ethyl-4-(4-ethyl-N-piperidino)cyclohexane;

1-(p-chlorophenyl)-1-dimethylamino-3-ethyl-4-(4-methylpiperazino)cyclohexane; and 1-(p-chlorophenyl)-1-dimethylamino-3-ethyl-4-(3-propyl-N-pyrrolidino)cyclohexane;

1-(p-chlorophenyl)-1-dimethylamino-3-n-propyl-4-methylethylaminocyclohexane;

1-(p-chlorophenyl)-1-dimethylamino-3-n-propyl-4-(N-allyl-N-propylamino)cyclohexane;

1-(p-chlorophenyl)-1-dimethylamino-3-n-propyl-4-(N-β-phenethyl-N-methylamino)cyclohexane;

1-(p-chlorophenyl)-1-dimethylamino-3-n-propyl-4-[N-(2-methoxy-4-chlorophenyl)-N-ethylamino]cyclohexane;

1-(p-chlorophenyl)-1-dimethylamino-3-n-propyl-4-(N-3,5-dimethylphenyl-N-propylamino)cyclohexane;

1-(p-chlorophenyl)-1-dimethylamino-3-n-propyl-4-N-morpholinocyclohexane;

1-(p-chlorophenyl)-1-dimethylamino-3-n-propyl-4-(4-ethyl-N-piperidino)cyclohexane;

1-(p-chlorophenyl)-1-dimethylamino-3-n-propyl-4-(4-methylpiperazino)cyclohexane; and 1-(p-chlorophenyl)-1-dimethylamino-3-n-propyl-4-(3-propyl-N-pyrrolidino)cyclohexane;

1-(p-chlorophenyl)-1-dimethylamino-3-n-butyl-4-methylethylaminocyclohexane;

1-(p-chlorophenyl)-1-dimethylamino-3-n-butyl-4-(N-allyl-N-propylamino)cyclohexane;

1-(p-chlorophenyl)-1-dimethylamino-3-n-butyl-4-(N-β-phenethyl-N-methylamino)cyclohexane;

1-(p-chlorophenyl)-1-dimethylamino-3-n-butyl-4-[N-(2-methoxy-4-chlorophenyl)-N-ethylamino]cyclohexane;

1-(p-chlorophenyl)-1-dimethylamino-3-n-butyl-4-(N-3,5-dimethylphenyl-N-propylamino)cyclohexane;

1-(p-chlorophenyl)-1-dimethylamino-3-n-butyl-4-N-morpholinocyclohexane;

1-(p-chlorophenyl)-1-dimethylamino-3-n-butyl-4-(4-ethyl-N-piperidino)cyclohexane;

1-(p-chlorophenyl)-1-dimethylamino-3-n-butyl-4-(4-methylpiperazino)cyclohexane; and 1-(p-chlorophenyl)-1-dimethylamino-3-n-butyl-4-(3-propyl-N-pyrrolidino)cyclohexane;

1-(p-chlorophenyl)-1-diethylamino-3-methyl-4-methylethylaminocyclohexane;

1-(p-chlorophenyl)-1-diethylamino-3-methyl-4-(N-allyl-N-propylamino)cyclohexane;

1-(p-chlorophenyl)-1-diethylamino-3-methyl-4-(N-$\beta$-phenethyl-N-methylamino)cyclohexane;

1-(p-chlorophenyl)-1-diethylamino-3-methyl-4-[N-(2-methoxy-4-chlorophenyl)-N-ethylamino]cyclohexane;

1-(p-chlorophenyl)-1-diethylamino-3-methyl-4-(N-3,5-dimethylphenyl-N-propylamino)cyclohexane;

1-(p-chlorophenyl)-1-diethylamino-3-methyl-4-N-morpholinecyclohexane;

1-(p-chlorophenyl)-1-diethylamino-3-methyl-4-(4-ethyl-N-piperidino)cyclohexane;

1-(p-chlorophenyl)-1-diethylamino-3-methyl-4-(4-methylpiperazino)cyclohexane; and 1-(p-chlorophenyl)-1-diethylamino-3-methyl-4-(3-propyl-N-pyrrolidino)cyclohexane;

1-(p-chlorophenyl)-1-di-n-propylamino-3-methyl-4-methylethylaminocyclohexane;

1-(p-chlorophenyl)-1-di-n-propylamino-3-methyl-4-(N-allyl-N-propylamino)cyclohexane;

1-(p-chlorophenyl)-1-di-n-propylamino-3-methyl-4-(N-$\beta$-phenethyl-N-methylamino)cyclohexane;

1-(p-chlorophenyl)-1-di-n-propylamino-3-methyl-4-[N-(2-methoxy-4-chlorophenyl)-N-ethylamino]cyclohexane;

1-(p-chlorophenyl)-1-di-n-propylamino-3-methyl-4-(N-3,5-dimethylphenyl-N-propylamino)cyclohexane;

1-(p-chlorophenyl)-1-di-n-propylamino-3-methyl-4-N-morpholinocyclohexane;

1-(p-chlorophenyl)-1-di-n-propylamino-3-methyl-4-(4-ethyl-N-piperidino)cyclohexane;

1-(p-chlorophenyl)-1-di-n-propylamino-3-methyl-4-(4-methylpiperazino)cyclohexane; and 1-(p-chlorophenyl)-1-di-n-propylamino-3-methyl-4-(3-propyl-N-pyrrolidino)cyclohexane;

1-(p-chlorophenyl)1-1-di-n-butylamino-3-methyl-4-methylethylaminocyclohexane;

1-(p-chlorophenyl)-1-di-n-butylamino-3-methyl-4-(N-allyl-N-propylamino)cyclohexane;

1-(p-chlorophenyl)-1-di-n-butylamino-3-methyl-4-(N-$\beta$-phenethyl-N-methylamino)cyclohexane;

1-(p-chlorophenyl)-1-di-n-butylamino-3-methyl-4-[N-(2-methoxy-4-chlorophenyl)-N-ethylamino]cyclohexane;

1-(p-chlorophenyl)-1-di-n-butylamino-3-methyl-4-(N-3,5-dimethylphenyl-N-propylamino)cyclohexane;

1-(p-chlorophenyl)-1-di-n-butylamino-3-methyl-4-N-morpholinocyclohexane;

1-(p-chlorophenyl)-1-di-n-butylamino-3-methyl-4-(4-ethyl-N-piperidino)cyclohexane;

1-(p-chlorophenyl)-1-di-n-butylamino-3-methyl-4-(4-methylpiperazino)cyclohexane; and 1-(p-chlorophenyl)-1-di-n-butylamino-3-methyl-4-(3-propyl-N-pyrrolidino)cyclohexane;

1-(p-chlorophenyl)-1-(N-propyl-N-2-butenylamino)-3-methyl-4-methylethylaminocyclohexane;

1-(p-chlorophenyl)-1-(N-propyl-N-2-butenylamino)-3-methyl-4-(N-allyl-N-propylamino)cyclohexane;

1-(p-chlorophenyl)-1-(N-propyl-N-2-butenylamino)-3-methyl-4-(N-$\beta$-phenethyl-N-methylamino)cyclohexane;

1-(p-chlorophenyl)-1-(N-propyl-N-2-butenylamino)-3-methyl-4-[N-(2-methoxy-4-chlorophenyl)-N-ethylamino]cyclohexane;

1-(p-chlorophenyl)-1-(N-propyl-N-2-butenylamino)-3-methyl-4-(N-3,5-dimethylphenyl-N-propylamino)cyclohexane;

1-(p-chlorophenyl)-1-(N-propyl-N-2-butenylamino)-3-methyl-4-N-morpholinocyclohexane;

1-(p-chlorophenyl)-1-(N-propyl-N-2-butenylamino)-3-methyl-4-(4-ethyl-N-piperidino)cyclohexane;

1-(p-chlorophenyl)-1-(N-propyl-N-2-butenylamino)-3-methyl-4-(4-methylpiperazino)cyclohexane; and 1-(p-chlorophenyl)-1-(N-propyl-N-2-butenylamino)-3-methyl-4-(3-propyl-N-pyrrolidino)cyclohexane;

1-(p-chlorophenyl)-1-(N-methyl-N-cyclopropylamino)-3-methyl-4-methylethylaminocyclohexane;

1-(p-chlorophenyl)-1-(N-methyl-N-cyclopropylamino-3-methyl-4-(N-allyl-N-propylamino)cyclohexane;

1-(p-chlorophenyl)-1-(N-methyl-N-cyclopropylamino)-3-methyl-4-(N-$\beta$-phenethyl-N-methylamino)cyclohexane;

1-(p-chlorophenyl)-1-(N-methyl-N-cyclopropylamino)-3-methyl-4-[N-(2-methoxy-4-chlorophenyl)-N-ethylamino]cyclohexane;

1-(p-chlorophenyl)-1-(N-methyl-N-cyclopropylamino)-3-methyl-4-(N-3,5-dimethylphenyl-N-propylamino)-cyclohexane;

1-(p-chlorophenyl)-1-(N-methyl-N-cyclopropylamino)-3-methyl-4-N-morpholinocyclohexane;

1-(p-chlorophenyl)-1-(N-methyl-N-cyclopropylamino)-3-methyl-4-(4-ethyl-N-piperidino)cyclohexane;

1-(p-chlorophenyl)-1-(N-methyl-N-cyclopropylamino)-3-methyl-4-(4-methylpiperazino)cyclohexane; and 1-(p-chlorophenyl)-1-(N-methyl-N-cyclopropylamino)-3-methyl-4-(3-propyl-N-pyrrolidino)cyclohexane;

1-(p-chlorophenyl)-1-(N-allyl-N-cyclopropylmethylamino)-3-methyl-4-methylethylaminocyclohexane;

1-(p-chlorophenyl)-1-(N-allyl-N-cyclopropylmethylamino)-3-methyl-4-(N-allyl-N-propylamino)cyclohexane;

1-(p-chlorophenyl)-1-(N-allyl-N-cyclopropylmethylamino)-3-methyl-4-(N-$\beta$-phenethyl-N-methylamino)cyclohexane;

1-(p-chlorophenyl)-1-(N-allyl-N-cyclopropylmethylamino)-3-methyl-4-[N-(2-methoxy-4-chlorophenyl)-N-ethylamino]cyclohexane;

1-(p-chlorophenyl-1-(N-allyl-N-cyclopropylmethylamino)-3-methyl-4-(N-3,5-dimethylphenyl-N-propylamino)cyclohexane;

1-(p-chlorophenyl)-1-(N-allyl-N-cyclopropylmethylamino)-3-methyl-4-N-morpholinocyclohexane;

1-(p-chlorophenyl)-1-(N-allyl-N-cyclopropylmethylamino)-3-methyl-4-(4-ethyl-N-piperidino)cyclohexane;

1-(p-chlorophenyl)-1-(N-allyl-N-cyclopropylmethylamino)-3-methyl-4-(4-methylpiperazino)cyclohexane; and 1-(p-chlorophenyl)-1-(N-allyl-N-cyclopropylmethylamino)-3-methyl-4-(3-propyl-N-pyrrolidino)cyclohexane.

EXAMPLE 8

Following the procedure of Example 4 but separately substituting each of the compounds prepared in Preparation XI for 4-(p-chlorophenyl)-4-dimethylaminocyclohexanone, and
methylethylamine,
N-allyl-N-propylamine,
N-β-phenethyl-N-methylamine,
N-(2-methoxy-4-chlorophenyl)-N-ethylamine,
N-(3,4-dimethylphenyl)-N-propylamine,
morpholine,
4-ethylpiperidine,
4-methylpiperazine,
3-propylpyrrolidine for morpholine, and reacting each amine independently with each ketone, there are obtained the following compounds:

1-(p-methoxyphenyl)-1-dimethylamino-4-methylethylaminocyclohexane;
1-(p-methoxyphenyl)-1-dimethylamino-4-(N-allyl-N-propylamino)cyclohexane;
1-(p-methoxyphenyl)-1-dimethylamino-4-(N-β-phenethyl-N-methylamino)cyclohexane;
1-(p-methoxyphenyl)-1-dimethylamino-4[N-(2-methoxy-4-chlorophenyl)-N-ethylamino]cyclohexane;
1-p-methoxyphenyl)-1-dimethylamino-4-(N-3,5-dimethylphenyl-N-propylamino)cyclohexane;
1-(p-methoxyphenyl)-1-dimethylamino-4-N-morpholinocyclohexane;
1-(p-methoxyphenyl)-1-dimethylamino-4-(4-ethyl-N-piperidino)cyclohexane;
1-(p-methoxyphenyl)-1-dimethylamino-4-(4-methyl-piperazino)cyclohexane; and
1-(p-methoxyphenyl)-1-dimethylamino-4-(3-propyl-N-pyrrolidino)cyclohexane;
1-(o-methylphenyl)-1-dimethylamino-4-methylethylaminocyclohexane;
1-(o-methylphenyl)-1-dimethylamino-4-(N-allyl-N-propylamino)cyclohexane;
1-(o-methylphenyl)-1-dimethylamino-4-(N-β-phenethyl-N-methylamino)cyclohexane;
1-(o-methylphenyl)-1-dimethylamino-4-[N-(2-methoxy-4-chlorophenyl)-N-ethylamino]cyclohexane;
1-(o-methylphenyl)-1-dimethylamino-4-(N-3,5-dimethylphenyl-N-propylamino)cyclohexane;
1-O-methylphenyl)-1-dimethylamino-4-N-morpholinocyclohexane;
1-(o-methylphenyl)-1-dimethylamino-4-(4-ethyl-N-piperidino)cyclohexane;
1-(o-methylphenyl)-1-dimethylamino-4-(4-methyl-piperazino)cyclohexane; and
1-(o-methylphenyl)-1-dimethylamino-4-(3-propyl-N-pyrrolidino)cyclohexane;
1-(p-bromophenyl)-1-dimethylamino-4-methylethylaminocyclohexane;
1-(p-bromophenyl)-1-dimethylamino-4-(N-allyl-N-propylamino)cyclohexane;
1-(p-bromophenyl)-1-dimethylamino-4-(N-β-phenethyl-N-methylamino)cyclohexane;
1-(p-bromophenyl)-1-dimethylamino-4-[N-(2-methoxy-4-chlorophenyl)-N-ethylamino]cyclohexane;
1-(p-bromophenyl)-1-dimethylamino-4-(N-3,5-dimethylphenyl-N-propylamino)cyclohexane;
1-(p-bromophenyl)-1-dimethylamino-4-N-morpholinocyclohexane;
1-(p-bromophenyl)-1-dimethylamino-4-(4-ethyl-N-piperidino)cyclohexane;
1-(p-bromophenyl)-1-dimethylamino-4-(4-methyl-piperazino)cyclohexane;
1-(p-bromophenyl)-1-dimethylamino-4-(3-propyl-N-pyrrolidino)cyclohexane;

1-(p-ethoxyphenyl)-1-dimethylamino-4-methylethylaminocyclohexane;
1-(p-ethoxyphenyl)-1-dimethylamino-4-(N-allyl-N-propylamino)cyclohexane;
1-(p-ethoxyphenyl)-1-dimethylamino-4-(N-β-phenethyl-N-methylaminocyclohexane;
1-(p-ethoxyphenyl)-1-dimethylamino-4-[N-(2-methoxy-4-chlorophenyl)-N-ethylamino]cyclohexane;
1-(p-ethoxyphenyl)-1-dimethylamino-4-(N-3,5-dimethylphenyl-N-propylamino)cyclohexane;
1-(p-ethoxyphenyl)-1-dimethylamino-4-N-morpholinocyclohexane;
1-(p-ethoxyphenyl)-1-dimethylamino-4-(4-ethyl-N-piperidino)cyclohexane;
1-(p-ethoxyphenyl)-1-dimethylamino-4-(4-methyl-piperazino)cyclohexane; and
1-(p-ethoxyphenyl)-1-dimethylamino-4-(3-propyl-N-pyrrolidino)cyclohexane;
1-(m-benzyloxyphenyl)-1-dimethylamino-4-methylethylaminocyclohexane;
1-(m-benzyloxyphenyl)-1-dimethylamino-4-(N-allyl-N-propylamino)cyclohexane;
1-(m-benzyloxyphenyl)-1-dimethylamino-4-(N-β-phenethyl-N-methylamino)cyclohexane;
1-(m-benzyloxyphenyl)-1-dimethylamino-4-[N-(2-methoxy-4-chlorophenyl)-N-ethylamino]cyclohexane;
1-(m-benzyloxyphenyl)-1-dimethylamino-4-(N-3,5-dimethylphenyl-N-propylamino)cyclohexane;
1-(m-benzyloxyphenyl)-1-dimethylamino-4-N-morpholinocyclohexane;
1-(m-benzyloxyphenyl)-1-dimethylamino-4-(4-ethyl-N-piperidino)cyclohexane;
1-(m-benzyloxyphenyl)-1-dimethylamino-4-(4-methyl-piperazino)cyclohexane; and
1-(m-benzyloxyphenyl)-1-dimethylamino-4-(3-propyl-N-pyrrolidino)cyclohexane;
1-(2,4-diethylphenyl)-1-dimethylamino-4-methylethylaminocyclohexane;
1-(2,4-diethylphenyl)-1-dimethylamino-4-(N-allyl-N-propylamino)cyclohexane;
1-(2,4-diethylphenyl)-1-dimethylamino-4-(N-β-phenethyl-N-methylamino)cyclohexane;
1-(2,4-diethylphenyl)-1-dimethylamino-4-[N-(2-methoxy-4-chlorophenyl)-N-ethylamino]cyclohexane;
1-(2,4-diethylphenyl)-1-dimethylamino-4-(N-3,5-dimethylphenyl-N-propylamino)cyclohexane;
1-(2,4-diethylphenyl)-1-dimethylamino-4N-morpholinocyclohexane;
1-(2,4-diethylphenyl)-1-dimethylamino-4-(4-ethyl-N-piperidino)cyclohexane;
1-(2,4-diethylphenyl)-1-dimethylamino-4-(4-methyl-piperazino)cyclohexane; and
1-(2,4-diethylphenyl)-1-dimethylamino-4-(3-propyl-N-pyrrolidino)cyclohexane;
1-(3,5-dichlorophenyl)-1-dimethylamino-4-methylethylaminocyclohexane;
1-(3,5-dichlorophenyl)-1-dimethylamino-4-(N-allyl-N-propylamino)cyclohexane;
1-(3,5-dichlorophenyl)-1-dimethylamino-4-(N-β-phenethyl-N-methylamino)cyclohexane;
1-(3,5-dichlorophenyl)-1-dimethylamino-4-[N-(2-methoxy-4-chlorophenyl)-N-ethylamino]cyclohexane;
1-(3,5-dichlorophenyl)-1-dimethylamino-4-(N-3,5-dimethylphenyl-N-propylamino)cyclohexane;

1-(3,5-dichlorophenyl)-1-dimethylamino-4-N-morpholinocyclohexane;
1-(3,5-dichlorophenyl)-1-dimethylamino-4-(4-ethyl-N-piperidino)cyclohexane;
1-(3,5-dichlorophenyl)-1-dimethylamino-4-(4-methylpiperazino)cyclohexane; and
1-(3,5-dichlorophenyl)-1-dimethylamino-4-(3-propyl-N-pyrrolidino)cyclohexane;
1-(3-methoxy-4-chlorophenyl)-1-dimethylamino-4-methylethylaminocyclohexane;
2-(3-methoxy-4-chlorophenyl)-10dimethylamino-4-(N-allyl-N-propylamino)cyclohexane;
1-(3-methoxy-4-chlorophenyl)-1-dimethylamino-4-(N-β-phenethyl-N-methylamino)cyclohexane;
1-(3-methoxy-4-chlorophenyl)-1-dimethylamino-4-[N-(2-methoxy-4-chlorophenyl)-N-ethylamino]cyclohexane;
1-(3-methoxy-4-chlorophenyl)-1-dimethylamino-4-(N-3,5-dimethylphenyl-N-propylamino)cyclohexane;
1-(3-methoxy-4-chlorophenyl)-1-dimethylamino-4N-morpholinocyclohexane;
1-(3-methoxy-4-chlorophenyl)-1-dimethylamino-4-(4-ethyl-N-piperidino)cyclohexane;
1-(3-methoxy-4-chlorophenyl)-1-dimethylamino-4-(4-methylpiperazino)cyclohexane; and
1-(3-methoxy-4-chlorophenyl)-1-dimethylamino-4-(3-propyl-N-pyrrolidino)cyclohexane;
1-(2-methyl-4-n-butylphenyl)-1-dimethylamino-4-methylethylaminocyclohexane;
1-(2-methyl-4-n-butylphenyl)-1-dimethylamino-4-(N-allyl-N-propylamino)cyclohexane;
1-(2-methyl-4-n-butylphenyl)-1-dimethylamino-4-(N-β-phenethyl-N-methylamino)cyclohexane;
1-(2-methyl-4-n-butylphenyl)-1-dimethylamino-4-[N-(2-methoxy-4-chlorophenyl)-N-ethylamino]cyclohexane;
1-(2-methy-4-n-butylphenyl)-1-dimethylamino-4-(N-3,5-dimethylphenyl-N-propylamino)cyclohexane;
1-(2-methyl-4-n-butylphenyl)-1-dimethylamino-4-N-morpholinocyclohexane;
1-(2-methyl-4-n-butylphenyl)-1-dimethylamino-4-(4-ethyl-N-piperidino)cyclohexane;
1-(2-methyl-4-n-butylphenyl)-1-dimethylamino-4-(4-methylpiperazino)cyclohexane; and
1-(2-methyl-4-n-butylphenyl)-1-dimethylamino-4-(3-propyl-N-pyrrolidino)cyclohexane;

EXAMPLE 9

Synthesis of
1-(m-hydroxyphenyl)-1-dimethylamino-4-N-morpholinocyclohexane

Part a

Following the procedure of Example 4 but substituting 4-(m-methoxyphenyl)-4-dimethylaminocyclohexanone (prepared as in Preparation V) for 4-(p-chlorophenyl)-4-dimethylaminocyclohexanone there is obtained 1-(m-methoxyphenyl)-1-dimethylamino-4-morpholinocyclohexane.

Part b

Following the procedure of Preparation VI, Part a, but substituting 1-dimethylamino-1-(m-methoxyphenyl)-4-morpholinocyclohexane (prepared in Part a, above) for 4-cyano-4-(m-anisyl)cyclohexanone [same as 4-(methoxyphenyl)-4-cyanocyclohexanone)]there is obtained 1-(m-hydroxyphenyl)-1-dimethylamino-4-morpholinocyclohexane.

EXAMPLE 10

Preparation of
1-(m-hydroxyphenyl)-1-(n-butylmethylamino)-4-morpholinocyclohexane Part a Following the procedure of Example 4 but substituting 4-(n-butylmethylamino)-4-(m-benzyloxyphenyl)cyclohexanone (prepared in Preparation VI, part g) for 4-dimethylamino-4-p-chlorophenyl)cyclohexanone, there is obtained 1-(m-benzyloxyphenyl)-1-(n-butylmethylamino)-4-morpholinocyclohexane.

Part b

Following the procedure of Preparation VI, Part h, but substituting 1-(m-benzyloxyphenyl)-1-(n-butylmethylamino)-4-morpholinocyclohexane for 4-(m-benzyloxyphenyl)-4-(n-butylmethylamino)cyclohexanone there is obtained 1-(m-hydroxyphenyl)-1-(n-butylmethylamino)4-morpholinocyclohexane.

EXAMPLE 11

Following the procedure of Example 9, Parts a and b, but initially substituting methylethylamine,
N-allyl-N-propylamine,
N-β-phenethyl-N-methylamine,
N-(2-methoxy-4-chlorophenyl)-N-ethylamine,
N-3,5-dimethylphenyl-N-propylamine,
4-ethylpiperidine,
4-methylpiperazine,
3-propylpyrrolidine for morpholine, there are obtained:
1-(m-hydroxyphenyl)-1-dimethylamino-4-methylethylaminocyclohexane;
1-(m-hydroxyphenyl)-1-dimethylamino-4-(N-allyl-N-propyl)aminocyclohexane;
1-(m-hydroxyphenyl)-1-dimethylamino-4-(N-β-phenethyl-N-methylamino)cyclohexane;
1-(m-hydroxyphenyl)-1-dimethylamino-4-[N-(2-methoxy-4-chlorophenyl)-N-ethylamino]cyclohexane;
1-(m-hydroxyphenyl)-1-dimethylamino-4-(N-3,5-dimethylphenyl-N-propylamino)cyclohexane;
1-(m-hydroxyphenyl)-1-dimethylamino-4-(4-ethyl-N-piperidino)cyclohexane;
1-(m-hydroxyphenyl)-1-dimethylamino-4-(4-methylpiperazino)cyclohexane; and
1-(m-hydroxyphenyl)-1-dimethylamino-4-(3-propyl-N-pyrrolidino)cyclohexane, respectively.

EXAMPLE 12

Following the procedure of Example 10, Parts a and b, but initially substituting
methylethylamine,
N-allyl-N-propylamine,
N-β
N-(2-methoxy-4-chlorophenyl)-N-ethylamine,
N-3,5-dimethylphenyl-N-propylamine,
4-ethylpiperidine,
4-methylpiperazine,
3-propylpyrrolidine for morpholine, there are obtained:
1-(m-hydroxyphenyl)-1-n-butylmethylamino-4-methylethylaminocyclohexane;
1-(m-hydroxyphenyl)-1-n-butylmethylamino-4-(N-allyl-N-propyl)aminocyclohexane;
1-(m-hydroxyphenyl)-1-n-butylmethylamino-4-(N-β-phenethyl-N-methylamino)cyclohexane;

1-(m-hydroxyphenyl)-1-n-butylmethylamino-4-]N-(2-methoxy-4-chlorophenyl)-N-ethylamino]cyclohexane;

1-(m-hydroxyphenyl)-1-n-butylmethylamino-4-(N-3,5-dimethylphenyl-N-propylamino)cyclohexane;

1-(m-hydroxyphenyl)-1-n-butylmethylamino-4-(4-ethyl-N-piperidino)cyclohexane;

1-(m-hydroxyphenyl)-1-n-butylmethylamino-4-(4-methylpiperazine)cyclohexane; and 1-(m-hydroxyphenyl)-1-n-butylmethylamino-4-(3-propyl-N-pyrrolidino)cyclohexane, respectively.

EXAMPLE 13

Part a

Following the procedure of preparation VIIA but substituting 4-(m-benzyloxyphenyl)-4-(n-butylmethylamino)-cyclohexanone (prepared according to Preparation VI) for 4-(p-chlorophenyl)-4-dimethylaminocyclohexanone there is obtained 4-(m-benzyloxyphenyl)-4-(n-butylmethylamino)-2-methylcyclohexanone.

Part b

Following the procedure of Example 10, Parts a and b but substituting 4-(m-benzyloxyphenyl)-4-n-butylmethylamino-2-methylcyclohexanone for 4-(m-benzyloxyphenyl)-4-n-butylmethylaminocyclohexanone there is obtained 1-(m-hydroxyphenyl)-1-n-butylmethylamino-3-methyl-4-morpholinocyclohexane.

EXAMPLE 14

Following the procedure of Example 10, Parts a and b but separately substituting each of the compounds prepared in Preparation XII for 4-(methyl-n-butylamino)-4-(m-benzyloxyphenyl)cyclohexanone initially and each of the following amines:
methylethylamine,
N-β-phenethyl-N-methylamine,
N-β-phenethyl-N-methylamine,
N-(2-methoxy-4-chlorophenyl)-N-ethylamine,
N-3,5-dimethylphenyl-N-propylamine,
morpholine,
4-ethylpiperidine,
4-methylpiperazine,
3-propylpyrrolidine for morpholine, and reacting each amine independently with each ketone, there are obtained the following compounds:

1-(methylethylamino)-1-(m-hydroxyphenyl)-4-methylethylaminocyclohexane;

1-(methylethylamino)-1-(m-hydroxyphenyl)-4-(N-allyl-N-propylamino)cyclohexane;

1-(methylethylamino)-1-(m-hydroxyphenyl)-4-(N-β-phenethyl-N-methylamino)cyclohexane;

1-(methylethylamino)-1-(m-hydroxyphenyl)-4-[N-(2-methoxy-4-chlorophenyl)-N-ethylamino]cyclohexane;

1-(methylethylamino)-1-(m-hydroxyphenyl)-4-(N-3,5-dimethylphenyl-N-propylamino)cyclohexane;

1-(methylethylamino)-1-(m-hydroxyphenyl)-4-N-morpholinocyclohexane;

1-(methylethylamino)-1-(m-hydroxyphenyl)-4-(4-ethyl-N-piperidino)cyclohexane;

1-(methylethylamino)-1-(m-hydroxyphenyl)-4-(4-methyl-piperazino)cyclohexane;

1-(methylethylamino)-1-(m-hydroxyphenyl)-4-(3-propyl-N-pyrrolidino)cyclohexane;

1-(methyl-n-propylamino)-1-(m-hydroxyphenyl)-4-methylethylaminocyclohexane;

1-(methyl-n-propylamino)-1-(m-hydroxyphenyl)-4-(N-allyl-N-propylamino)cyclohexane;

1-(methyl-n-propylamino)-1-(m-hydroxyphenyl)-4-(N-β-phenethyl-N-methylamino)cyclohexane;

1-(methyl-n-propylamino)-1-(m-hydroxyphenyl)-4-[N-(2-methoxy-4-chlorophenyl)-N-ethylamino]cyclohexane;

1-(methyl-n-propylamino)-1-(m-hydroxyphenyl)-4-(N-3,5-dimethylphenyl-N-propylamino)cyclohexane;

1-(methyl-n-propylamino)-1-(m-hydroxyphenyl)-4-N-morpholinocyclohexane;

1-(methyl-n-propylamino)-1-(m-hydroxyphenyl)-4-(4-ethyl-N-piperidino)cyclohexane;

1-(methyl-n-propylamino)-1-(m-hydroxyphenyl)-4-(4-methylpiperazino)cyclohexane; and 1-(methyl-n-propylamino)-1-(m-hydroxyphenyl)-4-(3-propyl-N-pyrrolidino)cyclohexane;

1-(n-pentylmethylamino)-1-(m-hydroxyphenyl)-4-methylethylaminocyclohexane;

1-(n-pentylmethylamino)-1-(m-hydroxyphenyl)-4-(N-allyl-N-propylamino)cyclohexane;

1-(n-pentylmethylamino)-1-(m-hydroxyphenyl)-4-(N-β-phenethyl-N-methylaminocyclohexane;

1-(n-pentylmethylamino)-1-(m-hydroxyphenyl)-4-[N-(2-methoxy-4-chlorophenyl)-N-ethylamino]cyclohexane;

1-(n-pentylmethylamino)-1-(m-hydroxyphenyl)-4-(N-3,5-dimethylphenyl-N-propylamino)cyclohexane;

1-(n-pentylmethylamino)-1-(m-hydroxyphenyl)-4-N-morpholinocyclohexane;

1-(n-pentylmethylamino)-1-(m-hydroxyphenyl)-4-(4-ethyl-N-piperidino)cyclohexane;

1-(n-pentylmethylamino)-1-(m-hydroxyphenyl)-4-(4-methylpiperazino)cyclohexane; and 1-(n-pentylmethylamino)-1-(m-hydroxyphenyl)-4-(3-propyl-N-pyrrolidino)cyclohexane;

1-(N-methyl-N-cyclopropylmethylamino)-1-(m-hydroxyphenyl)-4-methylethylaminocyclohexane;

1-(N-methyl-N-cyclopropylmethylamino)-1-(m-hydroxyphenyl)-4-(N-allyl-N-propylamino)cyclohexane;

1-(N-methyl-N-cyclopropylmethylamino)-1-(m-hydroxyphenyl)-4-(N-β-phenethyl-N-methylamino)cyclohexane;

1-(N-methyl-N-cyclopropylmethylamino)-1-(m-hydroxyphenyl)-4-[N-(2-methoxy-4-chlorophenyl)-N-ethylamino]-cyclohexane;

1-(N-methyl-N-cyclopropylmethylamino)-1-(m-hydroxyphenyl)-4-(N-3,5-dimethylphenyl-N-propylamino)cyclohexane;

1-(N-methyl-N-cyclopropylmethylamino)-1-(m-hydroxyphenyl)-4-N-morpholinocyclohexane;

1-(N-methyl-N-cyclopropylmethylamino)-1-(m-hydroxyphenyl)-4-(4-ethyl-N-piperidino)cyclohexane;

1-(N-methyl-N-cyclopropylmethylamino)-1-(m-hydroxyphenyl)-4-(4-methylpiperazino)cyclohexane; and 1-(N-methyl-N-cyclopropylmethylamino)-1-(m-hydroxyphenyl)-4-(3-propyl-N-pyrrolidino)cyclohexane;

1-(N-β-cyclohexylethyl-N-methylamino)-1-(m-hydroxyphenyl)-4-methylethylaminocyclohexane;

1-(N-β-cyclohexylethyl-N-methylamino)-1-(m-hydroxyphenyl)-4-(N-allyl-N-propylamino)cyclohexane;

1-(N-β-cyclohexylethyl-N-methylamino)-1-(m-hydroxyphenyl)-4-(N-β-phenethyl-N-methylamino)cyclohexane;

1-(N-β-cyclohexylethyl-N-methylamino)-1-(m-hydroxyphenyl)-4-[N-(2-methoxy-4-chlorophenyl)-N-ethylamino]-cyclohexane;

1-(N-β-cyclohexylethyl-N-methylamino)-1-(m-hydroxyphenyl)-4-(N-3,5-dimethylphenyl-N-propylamino)-cyclohexane;

1-(N-β-cyclohexylethyl-N-methylamino)-1-(m-hydroxyphenyl)-4-N-morpholinocyclohexane;

1-(N-β-cyclohexylethyl-N-methylamino)-1-(m-hydroxyphenyl)-4-(3-ethyl-N-piperidino)cyclohexane;

1-(N-β-cyclohexylethyl-N-methylamino)-1-(m-hydroxyphenyl)-4-(4-methylpiperazino)cyclohexane;

1-(N-β-cyclohexylethyl-N-methylamino)-1-(m-hydroxyphenyl)-4-(3-propyl-N-pyrrolidino)cyclohexane;

1-(N-benzyl-N-methylamino)-1-(m-hydroxyphenyl)-4-methylethylaminocyclohexane;

1-(N-benzyl-N-methylamino)-1-(m-hydroxyphenyl)-4-(N-allyl-N-propylamino)cyclohexane;

1-(N-benzyl-N-methylamino)-1-(m-hydroxyphenyl)-4-(N-β-phenethyl-N-methylamino)cyclohexane;

1-(N-benzyl-N-methylamino)-1-(m-hydroxyphenyl)-4-[N-(2-methoxy-4-chlorophenyl)-N-ethylamino]cyclohexane;

1-(N-benzyl-N-methylamino)-1-(m-hydroxyphenyl)-4-(N-3,4-dimethylphenyl-N-propylamino)cyclohexane;

1-(N-benzyl-N-methylamino)-1-(m-hydroxyphenyl)-4-N-morpholinocyclohexane;

1-(N-benzyl-N-methylamino)-1-(m-hydroxyphenyl)-4-(4-ethyl-N-piperidino)cyclohexane;

1-(N-benzyl-N-methylamino)-1-(m-hydroxyphenyl)-4-(4-methylpiperazino)cyclohexane;

1-(N-benzyl-N-methylamino)-1-(m-hydroxyphenyl)-4-(3-propyl-N-pyrrolidino)cyclohexane, respectively.

EXAMPLE 15

Preparation of
1-(m-hydroxyphenyl)-1-(methyl-n-butylamino)-4-(N-pyrrolidinyl)cyclohexane Following the procedure of Example 2 but substituting 1.28 gm. (0.045 mole) of 4-(m-hydroxyphenyl)-4-(methyl-n-butylamino)cyclohexanone (prepared in Preparation VI, Part i) for 4-phenyl-4-dimethylaminocyclohexanone there is obtained 0.34 gm. of 1-(m-hydroxyphenyl)-1-(methyl-n-butylamino)-4-(N-pyrrolidinyl)cyclohexane having a m.p. 174°–178° C.

Analysis: Calc'd. for $C_{21}H_{34}N_2O$: C, 76.31; H, 10.37; N, 8.48. Found: C, 75.97; H, 10.43; N, 8.55.

Further elution of the chromatography column (as in Example 2) followed by recrystallization from Skellysolve B ® gives 0.11 gm. of the more polar isomer of the title compound having a m.p. 140°–144° C.

Analysis: Calc'd. for $C_{21}H_{34}N_2O$: C, 76.31; H, 10.37; N, 8.48. Found: C, 76.22; H, 10.46; N, 8.45.

EXAMPLE 16

Following the procedure of Preparation VI, Part j, but substituting 1-(m-hydroxyphenyl)-1-(methyl-n-butylamino)-4-(N-morpholinocyclohexane (prepared in Example 9b) for 4-(m-hydroxyphenyl)-4-(methyl-n-butylamino)cyclohexanone there is obtained 1-(m-acetoxyphenyl)-1-(methyl-n-butylamino)-4-(N-morpholino)cyclohexane.

EXAMPLE 17

Preparation of
1-(m-methoxyphenyl)-1-(methyl-n-butylamino)-4-N-pyrrolidinylcyclohexane Part a Following the procedure of Preparation V, Part i, but substituting 4-(m-methoxyphenyl)-4-methylaminocyclohexanone ethylene ketal hydrochloride (prepared in Preparation V, Part g) for 4-(m-methoxyphenyl)-4-dimethylaminocyclohexanone ethylene ketal hydrochloride there is obtained 4-(m-methoxyphenyl)-4-methylaminocyclohexanone.

Part b

Following the procedure of Preparation VI, part f, but substituting 4-(m-methoxyphenyl)-4-methylaminocyclohexanone for 4-(m-benzyloxyphenyl)-4-methylaminocyclohexanone ethylene ketal there is obtained, after workup, the corresponding 4-(m-methoxyphenyl)-4-(methyl-n-butylamino)-cyclohexanone.

Part c

A mixture of 2.0 gm. (6.9 mmole) of the ketone from part b, 0.54 gm. (0.63 ml.) pyrrolidine, and 50 mg. of p-toluenesulfonic acid in 40 ml. benzene is heated at reflux temperature under a Dean-Stark trap for 3 hours. The solvent is then removed under vacuum. To a solution of the residue in 30 ml. of THF there is added a slurry of 0.30 gm. of sodium borohydride in 10 ml. of absolute ethanol. Following 13 hours' stirring at reflux, the bulk of the solvent is removed in vacuo; the residue is partitioned between water and diethyl ether; the organic layer is washed with water and brine and taken to dryness. The residue is chromatographed on a 250 ml. silica gel column, eluted initially with a solvent mixture of 0.5% $NH_4OH$:5% methanol:$CH_2Cl_2$ followed by 0.5% $NH_4OH$:10% MeOH: $CH_2Cl_2$. The material obtained is converted to the hydroiodide salt and recrystallized from $CH_2Cl_2$:ethyl acetate solvent mixture to yield 0.88 gm. (22% yield) of the title compound (less polar isomer), m.p. 181°–184° C.

Analysis: Calc'd. for $C_{22}H_{36}N_2O\cdot 2HI$: C, 44.01; H, 6.38; N, 4.67; I, 42.28. Found: C, 43.87; H, 6.63; N, 4.87; I, 42.71.

Further elution of the silica gel column affords a second (the more polar) isomer which after recrystallization from $CH_2Cl_2$:ethyl acetate is converted to and isolated as its dihydrochloride salt (0.38 gm., 9.4% yield) m.p. 207°–209° C.

Analysis: Calc'd. for $C_{22}H_{36}N_2O\cdot 2HCl$: Cl, 16.99. Found: Cl, 16.69.

EXAMPLE 18

Following the procedure of Example 16, but substituting propionic anhydride and butyric anhydride for acetic anhydride there are prepared the corresponding 1-(m-propionoxyphenyl)-1-(methyl-n-butylamino)-4-(N-morpholino)-cyclohexane and 1-(m-butyroxyphenyl)-1-(methyl-n-butylamino)-4-(N-morpholino)cyclohexane, respectively.

The compounds of the Formula I have analgetic activity and can be used for the relief of pain without loss of consciousness. The compounds can be used to treat the pain of headache, muscle spasm, arthritis and other musculoskeletal conditions, e.g., bursitis, relieve mild to moderate post-operative and post-partum pain; dysmenorrhea and pain of traumatic origin. Additionally, the compounds of Formula I can be administered for the treatment of severe pain, e.g., pain associated with adenocarcinoma, amputation of a limb, and third degree burns over a major portion of the body in animals and humans.

The dosage of the compound of the Formula I for analgetic purposes is from about 0.1 to about 7 mg./kg. body weight of the patient. The compounds of the Formula I are conveniently prepared in 5, 10, 25, 50, 75, 100, 250, and 500 mg. dosage units for administration for 1 to 4 times a day. Preferred unit dosages are from 0.3 to 3.5 mg./kg. body weight of the patient.

The compounds are administered orally, parenterally and rectally for systemic action.

The compositions of the present invention are presented for administration to humans and animals in unit dosage forms, such as tablets, capsules, pills, powders, granules, sterile parenteral solutions or suspensions, and oral solutions or suspensions, and oil-water emulsions containing suitable quantities of a compound of Formula I or its pharmacologically acceptable salts.

Pharmaceutical dosage unit forms are prepared in accordance with the subsequent general specific descriptions to provide from about 5 mg. to about 500 mg. of the essential active ingredient per dosage unit form (preferred 15–250 mg.).

Oral pharmaceutical dosage forms are either solid or liquid. The solid dosage forms are tablets, capsules, granules, and bulk powders. Types of oral tablets are, for example, compressed (including chewable and lozenge), tablet triturates, enteric-coated, sugar-coated, film-coated, and multiple compressed. Capsules are either hard or soft elastic gelatin. Granules and powders are either effervescent or non-effervescent.

Pharmaceutically acceptable substances utilized in compressed tablets are binders, lubricants, diluents, disintegrating agents, coloring agents, flavoring agents, flow inducing agents, and wetting agents. Tablet triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which usually four different layers of pharmaceutically acceptable substances have been applied. Film-coated tablets are compressed tablets which have been coated with a water soluble cellulose polymer. Multiple compressed tablets are compressed tablets made by more than one compression cycle utilizing the pharmaceutically acceptable substances previously mentioned. Coloring agents are utilized in the above dosage forms. Flavoring and sweetening agents are utilized in compressed tablets, tablet triturates, sugar coated, multiple compressed and chewable tablets. Flavoring and sweetening agents are especially useful in the formation of chewable tablets and lozenges.

Examples of binders include glucose solution (25–20%), acacia mucilage (10–20%), gelatin solution (10–20%), sucrose and starch paste. Lubricants include, for example, talc, starch, magnesium or calcium stearate, lycopodium and stearic acid. Diluents include, for example, lactose, sucrose, starch, kaolin, salt, mannitol and dicalcium phosphate. Disintegrating agents include, for example, corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumina hydrate. Sweetening agents include, for example, sucrose, lactose, mannitol, and artificial sweetening agents such as sodium cyclamate and saccharin, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monooleate, diethylene glycol monolaurate and polyoxyethylene laural ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets, include, for example, dextrin and gelatin. The second layer, an opaque zone, includes, for example, starch, talc, calcium carbonate, magnesium oxide and magnesium carbonate. The third layer, a translucaent zone, includes, for example, sucrose. The fourth layer, a glaze, includes, for example, beeswax, carnauba wax, or a mixture of these waxes. Film-coatings include, for example, hydroxyethylcellulose, sodium carboxymethylcellulose, polyethylene glycol 4000 and cellulose accetate phthalate.

Hard gelatin capsules, sizes 5 through 1000, are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastrointestinal intestinal tract, polyvinyl alcohol, ethyl cellulose and mixtures of beeswax, carnauba wax or bayberry wax with glyceryl monostearate.

Soft elastic gelatin capsules contain sufficient glycerine so that they are permanently flexible. Pharmaceutically acceptable liquid diluents used in soft elastic gelatin capsules are those which do not dissolve or harm the capsule and which are non-toxic, including, for example, corn oil, cottonseed oil, polysorbate 80, DMA and triacetin.

Pharmaceutically acceptable substances utilized in non-effervescent granules, for solution and/or suspension, include diluents, wetting agents, flavoring agents and coloring agents. Examples of diluents, wetting agents, flavoring agents and coloring agents include those previously exemplified.

Pharmaceutically acceptable substances utilized in effervescent granules and powders include organic acids, a source of carbon dioxide, diluents, wetting agents, flavoring agents and coloring agents.

Examples of organic acids include, for example, citric acid and tartaric acid. Sources of carbon dioxide include, for example, sodium bicarbonate and sodium carbonate. Examples of sweetening agents include, for example, sucrose, calcium cyclamate and saccharin. Examples of diluents, wetting agents and coloring agents include those previously exemplified.

Bulk powders have the compound of the Formula I uniformly dispersed throughout a pharmaceutically acceptable powdered carrier diluent. Examples of the diluent include those previously exemplified.

The individual oral solid pharmaceutical dosage forms, tablets and capsules, are packaged individually, unit-dose, or in quantity, multiple-dose containers, for example, bottles of 50, 100, 500, 1000, or 5000.

The amount of compound of the Formula I analog per dose unit is adjusted so that it provides the patient with an effective amount. The exact dose depends on the age, weight and condition of the patient or animal as is known in the art. For example, tablets and capsules are given in sufficient number and frequency to obtain the desired pharmacological effect.

The sustained release tablets and capsules provide an effective amount upon ingestion and continue to release a sufficient amount of the active material to keep the concentration at an effective level for increased periods of time, for example, 12 hours.

Non-effervescent granules and powders are packaged in predetermined amounts, such that when reconstituted with a specified quantity of an appropriate liquid vehicle, usually distilled water water, a solution and/or suspension results, providing a uniform concentration of the compound of the Formula I after shaking, if necessary. The concentration of the solution is such that a teaspoonful (5 ml.), a tablespoonful (one-half ounce or 15 ml.) or a fraction or a multiple thereof will provide an effective amount to produce the desired pharmacological effect. The exact dose depends on the age, weight and condition of the patient or animal, as is known in the art.

Effervescent granules and powders are packaged either in unit-dose, for example, tin foil packets, or in bulk, for example, in 4 oz. and 8 oz. amounts, such that a specific amount, either a unit-dose or, for example, a teaspoonful, tablespoonful or a fraction or a multiple thereof of bulk granules, when added to a specific amount of liquid vehicle, for example, water, yields a container of liquid dosage form to be ingested. The concentration of the active material in the granules is adjusted so that a specified amount when mixed with a specific amount of water yields an effective amount of the active material and produces the desired pharmacological effect. The exact amount of granules to be used depends on age, weight and condition of the patient as is known in the art.

Liquid oral dosage forms include, for example, aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water (o/w) or water-in-oil (w/o).

Elixirs are clear, sweetened, hydroalcoholic preparations. Pharmaceutically acceptable substances utilized in elixirs include, for example, solvents. Syrups are concentrated aqueous solutions of a sugar, for example, sucrose, and may contain a preservative. An emulsion is a two-phase system in which one liquid is dispersed in the form of small globules throughout another liquid. O/w emulsions are much preferred for oral administration over w/o emulsions. Pharmaceutically acceptable substances utilized in emulsions are non-aqueous liquids, emulsifying agents and preservatives. Suspensions utilize pharmaceutically acceptable suspending agents and preservatives. Pharmaceutically acceptable substances utilized in non-effervescent granules, to be reconstituted into a liquid oral dosage form, include, for example, diluents, sweeteners, and wetting agents. Pharmaceutically acceptable substances utilized in effervescent granules, to be reconstituted into a liquid oral dosage form, include, for example, organic acids and a source of carbon dioxide. Coloring and flavoring agents are utilized in all of the above dosage forms.

Solvents include, for example, glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include, for example, mineral oil and cottonseed oil. Examples of emulsifying agents include for example, gelatin, acacia, tragacanth, bentonite, and surfactants such as polyoxyethylene sorbitan monooleate. Suspending agents include, for example, sodium carboxymethylcellulose, pectin, tragacanth, Veegum and acacia. Diluents include, for example, lactose and sucrose. Sweetening agents include, for example, sucrose, syrups, glycerin, and artificial sweetening agents such as sodium cyclamate and saccharin. Wetting agents include, for example, propylene glycol monostearate, sorbitan momooleate, diethylene glycol monolaurate and polyoxyethylene lauryl ether. Organic acids include, for example, citric and tartaric acid. Sources of carbon dioxide include, for example, sodium bicarbonate and sodium carbonate. Coloring agents include, for example, any of the approved, certified water soluble FD and C dyes, and mixtures thereof. Flavoring agents include, for example, natural flavors extracted from plants such as fruits, and synthetic blends of compounds which produce a pleasant taste sensation.

The concentration of the compound of the Formula I throughout the solutions must be uniform. Upon shaking, the concentration of the compound of the Formula I throughout the emulsions and suspensions must be uniform.

The concentration of the compound of the Formula I is adjusted so that a teaspoonful (5 ml.), a tablespoonful (one-half ounce or 15 ml.) or a fraction or multiple thereof, will provide an effective amount to produce the desired pharmacological effect. The exact dose depends on the age, weight and condition of the patient or animal as is known in the art.

The liquid oral dosage forms may be packaged, for example, in unit-dose sizes of 5 ml. (teaspoonful), 10 ml., 15 ml. (tablespoonful) and 30 ml. (one ounce), and multiple dose containers, including, for example, 2 oz., 3 oz., 4 oz., 6 oz., 8 oz., pint, quart, and gallon sizes.

Parenteral administration includes intravenous, subcutaneous, intramuscular, and the like.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or non-aqueous.

Pharmaceutically acceptable substances utilized in parenteral preparations include aqueous vehicles, non-aqueous vehicles, antimicrobial agents, isotonic agents, buffers, antioxidants, local anesthetics, suspending and dispersing agents, emulsifying agents, sequestering or chelating agents and other pharmaceutical necessities.

Examples of aqueous vehicles include Sodium Chloride Injection, Ringers Injection, Isotonic (5 percent) Dextrose Injection, Sterile Water for Injection, Dextrose and Sodium Chloride Injection and Lactated Ringers Injection. Non-aqueous parenteral vehicles include fixed oils of vegetable origin, for example, cottonseed oil, corn oil, sesame oil and peanut oil. Antimicrobial agents in bacteriostatic or fungistatic concentrations must be added to parenteral preparations packaged in multiple-dose containers (vials) which include phenol or cresols, mercurials, benzyl alcohol, chlorobutanol, methyl and propyl p-hydroxybenzoic acid esters, thimerosal, benzalkonium chloride and benzethonium chloride. Isotonic agents include, for example, sodium chloride and dextrose. Buffers include, for example, ph phate and citrate. Antioxidants include, for example, sodium bisulfite. Local anesthetics include, for example, procaine hydrochloride. Suspending and dispersing agents include, for example, sodium carboxymethylcellulose, hydroxypropyl methylcellulose and polyvinylpyrrolidone. Emulsifying agents include, for example, Polysorbate 80 (Tween 80). A sequestering or chelating agent of metal ions include, for example, EDTA ethylenediaminetetraacetic acid). Pharmaceutical necessities include, for example, ethyl alcohol, polyethylene glycol and propylene glycol for water miscible vehicles and sodium hydroxide, hydrochloric acid, citric acid or lactic acid for pH adjustment.

The concentration of the pharmaceutically active ingredient is adjusted so that an injection, for example, 0.5 ml., 1.0 ml., 2.0 ml., and 5.0 ml. or an intraarterial or intravenous infusion, for example, 0.5 ml./min., 1.0 ml./min., 1.0 ml./min., and 2.0 ml./min. provides an effective amount to produce the desired pharmacological effect. The exact dose depends on the age, weight and condition of the patient or animal as is known in the art.

The unit-dose parenteral preparations are packaged, for example, in an ampul or a syringe with a needle. The multiple-dose package, for example, is a vial.

All preparations for parenteral administration must be sterile, as is known and practiced in the art.

Illustratively, intravenous or intraarterial infusion of a sterle aqueous solution containing an active material is an effective mode of administration. Another embodiment is a sterile aqueous or oily solution or suspension containing an active material injected as necessary to produce the desired pharmacological effect.

Pharmaceutical dosage forms for rectal administration are rectal suppositories, capsules, tablets for systemic effect.

Rectal suppositories as used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases or vehicles include, for example, cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include, for example, spermaceti and wax. Rectal suppositories may be prepared either by the compressed method or by molding. The usual weight of a rectal suppository is about 2.0 gm.

Tablets and capsules for rectal administration are manufactured utilizing the same pharmaceutically acceptable substance and by the same methods as for formulations for oral administration.

Rectal suppositories, tablets or capsules are packaged either individually, in unit-dose, or in quantity, multiple dose, for example, 2, 6, or 12.

The pharmaceutically therapeutically active compounds of the Formula I are administered orally, parenterally or rectally in unit-dosage forms or multiple dosage forms. Unit-dose forms as used in the specification and claims refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampuls and syringes (parenteral), individually packaged tablet or capsule (oral-solid) or individually packaged teaspoonful or tablespoonful (oral-liquid). Unit-dose forms may be administered in fractions or multiples thereof. A multiple-dose form is a plurality of identical unit-dosage forms packaged in a single container to be administered in segregated unit-dose form. Examples of multiple-dose forms include vials (parenteral), bottles of tablets or capsules (oral solid) or bottles of pints or gallons (oral-liquid). Hence, multiple dose form is a multiple of unit-doses which are not segregated in packaging. The specifications for the unit-dosage form and the multiple dosage form are dictated by and directly dependent on (a) the unique characteristics of the therapeutically active compound and the particular therapeutic effect to be achieved and (b) the limitations inherent in the art of compounding such a therapeutically active compound for therapeutic or prophylactic.

In addition to the administration of a compound of Formula I as the principal active ingredient of compositions for the treatment of the conditions described herein, the said compound can be included with other types of compounds to obtain advantageous combinations of properties. Such combinations include a compound of Formula I with other analgesics such as aspirin, phenacetin, acetaminophen, propoxyphen, pentazocine, codeine, meperidine, oxycodone, mefenamic acid, and ibuprofen; muscle relaxants such as methocarbamol, orphenadrine, carisoprodol, meprobamate, chlorphenesin carbamate, diazepam, chlordiazepoxide, and chlorzoxazone; analeptics such as caffeine, methylphenidate and pentylenetetrazol; corticosteroids such as methylprednisolone, prednisone, prednisolone and dexamethasone, antihistamines such as chlorpheniramine, cyproheptadine, promethazine and pyrilamine.

EXAMPLE 19

Capsules

One thousand two-piece hard gelatin capsules for oral use, each containing 5 mg. of 1-(p-chlorophenyl)-1-dimethylamino-4-(N-morpholino)cyclohexane are prepared from the following types and amounts of materials:

1-(p-chlorophenyl)-1-dimethylamino-4-(N-morpholino)-cyclohexane: 5 g.
Lactose: 150 g.
Corn starch: 25 g.
Talc: 20 g.
Magnesium stearate: 2.0 g.

The materials are thoroughly mixed and then encapsulated in the usual manner.

The foregoing capsules are useful for the treatment of headache in adult humans by the oral administration of 1 capsule every 4 hours.

Using the procedure above, capsules are similarly prepared containing 1-(p-chlorophenyl)-1-dimethylamino-4-(N-morpholino)cyclohexane in 50, 75, 100, and 200 mg. amounts by substituting 50, 75, 100, and 200 mg. of 1-(p-chlorophenyl)-1-dimethylamino-4-(N-morpholino)cyclohexane for the 5 gm. used above.

EXAMPLE 20

Capsules

One thousand two-piece hard gelatin capsules for oral use, each containing 50 mg. of 1-(p-chlorophenyl)-1-dimethylamino-4-(N-morpholino)cyclohexane and 325 mg. of aspirin, are prepared from the following types and amounts of ingredients:

1-(p-chlorophenyl)-1-dimethylamino-4-(N-morpholino)-cyclohexane: 50 g.
Aspirin: 325 g.
Talc: 35 g.
Magnesium stearate: 2.5 g.

The ingredients are thoroughly mixed and then encapsulated in the usual manner.

The foregoing capsules are useful for the treatment of headache in adult humans by the oral administration of 1 capsule every 6 hours.

EXAMPLE 21

Tablets

One thousand tablets for oral use, each containing 250 mg. of 1-(p-chlorophenyl)-2-dimethylamino-4-(N-morpholino)cyclohexane are prepared from the following types and amounts of materials:

1-(p-chlorophenyl)-1-dimethylamino-4-(N-morpholino)cyclohexane: 250 g.
Lactose: 125 g.
Corn starch: 65 g.
Magnesium stearate: 2.5 g.
Light liquid petrolatum: 3 g.

The ingredients are thoroughly mixed and slugged. The slugs are broken down by forcing through a number sixteen screen. The resulting granules are then compressed into tablets, each tablet containing 250 mg. of 1-(p-chlorophenyl)-1-dimethylamino-4-(N-morpholino)cyclohexane.

The foregoing tablets are useful for treatment of arthritic pain in adult humans by oral administration of 1 tablet every 12 hours.

EXAMPLE 22

Tablets

One thousand oral tablets, each containing 50 mg. of 1-(p-chlorophenyl)-1-dimethylamino-4-(N-morpholino)cyclohexane and a total of 400 mg. of chlorphenesin carbamate are prepared from the following types and amounts of materials:

1-(p-chlorophenyl)-1-dimethylamino-4-(N-morpholino)cyclohexane: 50 g.
Chlorphenes in Carbamate: 400 g.
Lactose: 50 g.
Corn starch: 50 g.
Calcium stearate: 2.5 g.
Light liquid petrolatum: 5 g.

The ingredients are thoroughly mixed and slugged. The slugs are broken down by forcing through a number sixteen screen. The resulting granules are then compressed into tablets, each containing 50 g. of 1-(p-chlorophenyl)-1-dimethylamino-4-(N-morpholino)cyclohexane and 400 mg. of chlorphenesin carbamate.

The foregoing tablets are useful for treatment of low back pain by the oral administraion of 1 tablet every 6 hours.

EXAMPLE 23

Oral syrup

One thousand ml. of an aqueous suspension for oral use, containing in each 5 ml. dose, 100 mg. of 1-(p-chlorophenyl)-1-dimethylamino-4-(N-morpholino)cyclohexane is prepared from the following types and amounts of ingredients:

1-(p-chlorophenyl)-1-dimethylamino-4-(N-morpholino)cyclohexane: 20 g.
Citric acid: 2 g.
Benzoic acid: 1 g.
Sucrose: 700 g.
Tragacanth: 5 g.
Lemon oil: 2 ml.
Deionized water q.s. 1000 ml.

The citric acid, benzoic acid, sucrose, tragacanth, and lemon oil are dispersed in sufficient water to make 850 ml. of solution. The 1-(p-chlorophenyl)-1-dimethylamino-4-(N-morpholino)cyclohexane is stirred into the syrup until uniformly distributed. Sufficient water is added to make 1000 ml.

The composition so prepared is useful in the treatment of headaches in adult humans at a dose of 1 teaspoonful 4 times a day.

EXAMPLE 24

Parenteral solution

A sterile aqueous solution for intramuscular use, containing in 1 ml. 25 g. of 1-(p-chlorophenyl)-1-dimethylamino-4-(N-morpholino)cyclohexane is prepared from the following types and amounts of materials:

1-(p-chlorophenyl)-1-dimethylamino-4-(N-morpholino)cyclohexane hydrochloride: 30 g.
Lidocaine hydrochloride: 4 g.
Methylparagen: 2.5 g.
Propylparaben: 0.17 g.
Water for injection q.s.: 1000 ml.

The ingredients are dissolved in the water and the solution sterilized by filtration. The sterile solution is filled into vials and the vials sealed.

EXAMPLE 25

Suppository, rectal

One thousand suppositories, each weighing 2.5 g. and containing 100 mg. of 1-(p-chlorophenyl)-1-dimethylamino-4-(N-morpholino)cyclohexane are prepared from the following types and amounts of ingredients:

1-(p-chlorophenyl)-1-dimethylamino-4-(N-morpholino)cyclohexane: 100 g.
Propylene glycol: 162.5 g.
Polyethylene glycol 4000 q.s.: 2300 g.

The 1-(p-chlorophenyl-1-dimethylamino-4-(N-morpholino)cyclohexane is added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The suppositories are useful in the treatment of headache by the insertion rectally of 1 suppository every 6 hours.

EXAMPLE 26

Compositions are similarly prepared following the procedure of the preceding Examples 19 through 25 substituting an equimolar amount each of
1-dimethylamino-4-N-morpholino-1-phenylcyclohexane;
1-dimethylamino-4-(N-piperidino)-1-phenylcyclohexane;
1-dimethylamino-4-(N-allyl-N-methylamino)-1-(p-chlorophenyl)cyclohexane;
1-(m-hydroxyphenyl)-1-dimethylamino-4-morpholinocyclohexane;
1-n-butylmethylamino-1-(p-chlorophenyl)-4-N-morpholinocyclohexane;
1-(m-hydroxyphenyl)-1-(n-butylmethylamino)-4-N-morpholinocyclohexane; or
1-(m-hydroxyphenyl)-1-(methyl-n-butylamino)-4-(N-pyrrolidinyl)cyclohexane or their pharmacologically acceptable salts for the 1-(p-chlorophenyl)-1-dimethylamino-4-(N-morpholino)cyclohexane of the Examples.

I claim:

1. A compound of the formula:

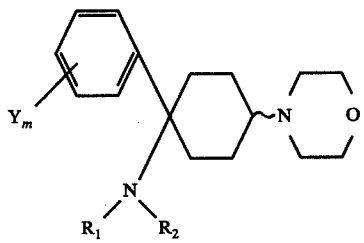

wherein Y is halogen, hydroxy or alkanoyloxy of from 2 to 5 carbon atoms, inclusive; $m$ is zero or one; and $R_1$ and $R_2$ are alkyl of from 1 to 4 carbon atoms, inclusive.

2. A compound according to claim 1 in its less polar form.

3. A compound according to claim 1 which is 1-phenyl-1-dimethylamino-4-N-morpholinocyclohexane.

4. A compound according to claim 1 which is 1-p-chlorophenyl-1-dimethylamino-4-morpholinocyclohexane.

5. A compound according to claim 1 which is 1-(m-hydroxyphenyl)-1-(methyl-n-butylamino)-4-N-morpholinocyclohexane.

6. A composition for relief of pain comprising a compound of the formula:

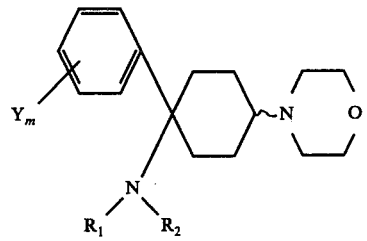

wherein Y is halogen, hydroxy or alkanoyloxy of from 2 to 5 carbon atoms, inclusive; $m$ is zero or one; and $R_1$ and $R_2$ are alkyl of from 1 to 5 carbon atoms, inclusive; or its pharmacologically acceptable salts, in association with a pharmaceutical carrier.

7. A composition according to claim 6 wherein the compound of the Formula is in its less polar form.

8. A composition according to claim 6, in unit dosage form where the concentration of the compound is from 5 to 500 mg. per dosage unit.

9. A composition according to claim 6 wherein the compound is 1-phenyl-1-dimethylamino-4-N-morpholinocyclohexane.

10. A composition according to claim 6 wherein the compound is 1-p-chlorophenyl-1-dimethylamino-4-N-morpholinocyclohexane.

11. A composition according to claim 6 wherein the compound is 1-(m-hydroxyphenyl)-1-(methyl-n-butylamino)-4-N-morpholinocyclohexane.

12. A method for relief of pain comprising the systemic administration to a human or animal of an analgetic amount of a compound of the formula:

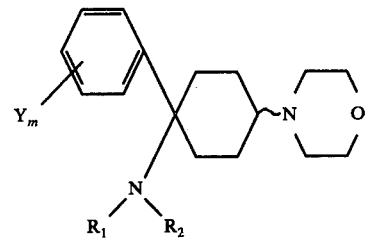

wherein Y is halogen, hydroxy or alkanoyloxy of from 2 to 5 carbon atoms, inclusive; $m$ is zero or one; and $R_1$ and $R_2$ are alkyl of from 1 to 4 carbon atoms, inclusive; or its pharmacologically acceptable acid addition salts.

13. The method of claim 12 wherein the compound is administered in an amount of from 0.1 mg. to 7 mg. per kg. body weight of the said human or animal.

14. The method of claim 12 wherein the compound administered is 1-phenyl-1-dimethylamino-4-N-morpholinocyclohexane.

15. The method of claim 12 where the compound administered is 1-p-chlorophenyl-1-dimethylamino-4-N-morpholinocyclohexane.

16. The method of claim 12 wherein the compound administered is 1-(m-hydroxyphenyl)-1-(methyl-n-butylamino)-4-N-morpholinocyclohexane.